United States Patent [19]

Samal et al.

[11] Patent Number: 5,278,062
[45] Date of Patent: Jan. 11, 1994

[54] PROTEOLYTIC ENZYMES

[75] Inventors: Babru B. Samal, Moor Park, Calif.; Yitzhak Stabinsky, Lawrenceville, N.J.

[73] Assignee: Amgen, Thousand Oaks, Calif.

[21] Appl. No.: 879,507

[22] Filed: May 1, 1992

Related U.S. Application Data

[63] Continuation of Ser. No. 696,337, May 1, 1991, abandoned, which is a continuation of Ser. No. 35,816, Apr. 3, 1987, abandoned.

[51] Int. Cl.$^5$ .................. C12N 9/58; C12N 15/11
[52] U.S. Cl. ..................................... 435/223; 435/219; 435/814; 435/911; 935/14; 252/174.12; 252/DIG. 12
[58] Field of Search ................ 435/223, 172.3, 320.1, 435/68, 70, 219; 530/350; 935/15, 68, 14; 252/174.12

[56] References Cited

PUBLICATIONS

Samal et ál. (1987) J. Cell. Biochem. 11C:237.
Samal et al. (1989) Gene 85:329-333.
Kolvenbach et al. (1990) Int. J. Peptide Protein Res. 36 387-391.
Samal et al. (1991) Enzyme Microl. Technol. 13:66-70.
Jany et al. (1986) FEBS Letters 199(2):139-144.
Dattagupta et al. (1975) J. Mol. Biol. 97:267-271.

*Primary Examiner*—Robert A. Wax
*Assistant Examiner*—Gabriele E. Bugaisky
*Attorney, Agent, or Firm*—Robert B. Winter

[57] ABSTRACT

This disclosure relates to a novel class of serine proteases isolated from a culture medium of fungus *Tritirachium album*. The serine proteases disclosed have a high degree of stability in detergent formulations.

In addition, this disclosure relates to a process for producing such serine proteases using recombinant techniques.

14 Claims, 23 Drawing Sheets

```
                10                      30                      50
     GAATTCATTG AACAAGACGC CGTTGTTACC ATCTCCGCCA CCCAGGAAGA CGCCCCATGG
     CTTAAGTAAC TTGTTCTGCG GCAACAATGG TAGAGGCGGT GGGTCCTTCT GCGGGGTACC 70                      90                     110
     GGTCTGGCCC GCATCTCCAG CCAGGAACCC GGCGGCACCA CTTATACCTA CGATGACTCT
     CCAGACCGGG CGTAGAGGTC GGTCCTTGGG CCGCCGTGGT GAATATGGAT GCTACTGAGA 130                     150                     170
     GCCGGTACAG GCACCTGCGC ATACATCATC GACACGGGCA TCTACACCAA CCACACTGTA
     CGGCCATGTC CGTGGACGCG TATGTAGTAG CTGTGCCCGT AGATGTGGTT GGTGTGACAT 190                     210                     230
     AGCTTCTCTC CGACCGAATC CGACCAGATC CCAAATGCTA ATAAATCGTA GGACTTTGGC
     TCGAAGAGAG GCTGGCTTAG GCTGGTCTAG GGTTTACGAT TATTTAGCAT CCTGAAACCG 250                     270                     290
     GGTCGTGCCA AGTTCCTCAA GAACTTTGCC GGTGACGGTC AAGACACCGA CGGCAACGGT
     CCAGCACGGT TCAAGGAGTT CTTGAAACGG CCACTGCCAG TTCTGTGGCT GCCGTTGCCA 310                     330                     350
     CACGGCACTC ACGTCGCCGG TACCGTGGGC GGAACAACCT ATGGTGTAGC CAAGAAGACA
     GTGCCGTGAG TGCAGCGGCC ATGGCACCCG CCTTGTTGGA TACCACATCG GTTCTTCTGT 370                     390                     410
     TCTCTCTTTG CTGTCAAGGT CCTCGACGCC AACGGTCAGG GCTCCAAGTA CGTTTTGTGT
     AGAGAGAAAC GACAGTTCCA GGAGCTGCGG TTGCCAGTCC CGAGGTTCAT GCAAAACACA 430                     450                     470
     CCTTTCCTCG TGTTCCACCA CCCTATCTTT CTCCTAATCG TCAATTGTAC TAACACATCG
     GGAAAGGAGC ACAAGGTGGT GGGATAGAAA GAGGATTAGC AGTTAACATG ATTGTGTAGC 490                     510                     530
     CCACCCAACA GCTCCGGCGT CATCGCAGGC ATGGACTTTG TTACCAAAGA CGCCTCGTCC
     GGTGGGTTGT CGAGGCCGCA GTAGCGTCCG TACCTGAAAC AATGGTTTCT GCGGAGCAGG 550                     570                     590
     CAAAACTGCC CCAAGGGCGT CGTAGTGAAC ATGTCGCTCG GTGGTCCCTC CTCCTCAGCC
     GTTTTGACGG GGTTCCCGCA GCATCACTTG TACAGCGAGC CACCAGGGAG GAGGAGTCGG
```

FIG. 1A

```
              610                630                650
    GTCAACCGCG CCGCCGCCGA AATCACCAGC GCAGGCCTCT TCCTCGCTGT CGCAGCCGGC
    CAGTTGGCGC GGCGGCGGCT TTAGTGGTCG CGTCCGGAGA AGGAGCGACA GCGTCGGCCG 670                690                710
    AACGAAGCCA CTGACGCCTC CTCGTCGTCC CCTGCGTCCG AAGAAAGCGC CTGCACTGTC
    TTGCTTCGGT GACTGCGGAG GAGCAGCAGG GGACGCAGGC TTCTTTCGCG GACGTGACAG 730                750                770
    GGCGCAACCG ACAAGACCGA CACGCTGGCC GAGTACTCCA ACTTTGGCAG CGTCGTTGAC
    CCGCGTTGGC TGTTCTGGCT GTGCGACCGG CTCATGAGGT TGAAACCGTC GCAGCAACTG 790                810                830
    CTCCTTGCTC CCGGTACGGA TATCAAGTCT ACCTGGAACG ACGGCCGCAC CAAGATTATT
    GAGGAACGAG GGCCATGCCT ATAGTTCAGA TGGACCTTGC TGCCGGCGTG GTTCTAATAA 850                870                890
    TCGGGCACGT CCATGGCTAG CCCACATGTT GCTGGACTGG GTGCGTACTT TTTGGGCCTT
    AGCCCGTGCA GGTACCGATC GGGTGTACAA CGACCTGACC CACGCATGAA AAACCCGGAA 910                930                950
    GGACAAAAGG TTCAGGGTCT TTGCGACTAC ATGGTTGAGA AGGGTCTCAA GGATGTCATT
    CCTGTTTTCC AAGTCCCAGA AACGCTGATG TACCAACTCT TCCCAGAGTT CCTACAGTAA 970                990                1010
    CAGAGTGTGC CCAGTGATAC TGCCAATGTT TTGATCAACA ATGGTGAGGG CTCGGCTTAG
    GTCTCACACG GGTCACTATG ACGGTTACAA AACTAGTTGT TACCACTCCC GAGCCGAATC 1030               1050
    ATGCGCTTAG AGTTGCATAC ATAGCCCGAC ATCGATGATG
    TACGCGAATC TCAACGTATG TATCGGGCTG TAGCTACTAC
```

FIG. 1B

```
              10                            30                           50
GAATTCATTG  AACAAGACGC  CGTTGTTACC  ATCTCCGCCA  CCCAGGAAGA  CGCCCCATGG
CTTAAGTAAC  TTGTTCTGCG  GCAACAATGG  TAGAGGCGGT  GGGTCCTTCT  GCGGGGTACC 70                            90                          110
GGTCTGGCCC  GCATCTCCAG  CCAGGAACCC  GGCGGCACCA  CTTATACCTA  CGATGACTCT
CCAGACCGGG  CGTAGAGGTC  GGTCCTTGGG  CCGCCGTGGT  GAATATGGAT  GCTACTGAGA 130                           150                          170
GCCGGTACAG  GCACCTGCGC  ATACATCATC  GACACGGGCA  TCTACACCAA  CCACACTGAC
CGGCCATGTC  CGTGGACGCG  TATGTAGTAG  CTGTGCCCGT  AGATGTGGTT  GGTGTGACTG 190                           210                          230
TTTGGCGGTC  GTGCCAAGTT  CCTCAAGAAC  TTTGCCGGTG  ACGGTCAAGA  CACCGACGGC
AAACCGCCAG  CACGGTTCAA  GGAGTTCTTG  AAACGGCCAC  TGCCAGTTCT  GTGGCTGCCG 250                           270                          290
AACGGTCACG  GCACTCACGT  CGCCGGTACC  GTGGGCGGAA  CAACCTATGG  TGTAGCCAAG
TTGCCAGTGC  CGTGAGTGCA  GCGGCCATGG  CACCCGCCTT  GTTGGATACC  ACATCGGTTC 310                           330                          350
AAGACATCTC  TCTTTGCTGT  CAAGGTCCTC  GACGCCAACG  GTCAGGGCTC  CAACTCCGGC
TTCTGTAGAG  AGAAACGACA  GTTCCAGGAG  CTGCGGTTGC  CAGTCCCGAG  GTTGAGGCCG 370                           390                          410
GTCATCGCAG  GCATGGACTT  TGTTACCAAA  GACGCCTCGT  CCCAAAACTG  CCCCAAGGGC
CAGTAGCGTC  CGTACCTGAA  ACAATGGTTT  CTGCGGAGCA  GGGTTTTGAC  GGGGTTCCCG 430                           450                          470
GTCGTAGTGA  ACATGTCGCT  CGGTGGTCCC  TCCTCCTCAG  CCGTCAACCG  CGCCGCCGCC
CAGCATCACT  TGTACAGCGA  GCCACCAGGG  AGGAGGAGTC  GGCAGTTGGC  GCGGCGGCGG 490                           510                          530
GAAATCACCA  GCGCAGGCCT  CTTCCTCGCT  GTCGCAGCCG  GCAACGAAGC  CACTGACGCC
CTTTAGTGGT  CGCGTCCGGA  GAAGGAGCGA  CAGCGTCGGC  CGTTGCTTCG  GTGACTGCGG 550                           570                          590
TCCTCGTCGT  CCCCTGCGTC  CGAAGAAAGC  GCCTGCACTG  TCGGCGCAAC  CGACAAGACC
AGGAGCAGCA  GGGGACGCAG  GCTTCTTTCG  CGGACGTGAC  AGCCGCGTTG  GCTGTTCTGG
```

FIG. 2A

```
         610                630                650
GACACGCTGG CCGAGTACTC CAACTTTGGC AGCGTCGTTG ACCTCCTTGC TCCCGGTACG
CTGTGCGACC GGCTCATGAG GTTGAAACCG TCGCAGCAAC TGGAGGAACG AGGGCCATGC 670                690                710
GATATCAAGT CTACCTGGAA CGACGGCCGC ACCAAGATTA TTTCGGGCAC GTCCATGGCT
CTATAGTTCA GATGGACCTT GCTGCCGGCG TGGTTCTAAT AAAGCCCGTG CAGGTACCGA 730                750                770
AGCCCACATG TTGCTGGACT GGGTGCGTAC TTTTTGGGCC TTGGACAAAA GGTTCAGGGT
TCGGGTGTAC AACGACCTGA CCCACGCATG AAAAACCCGG AACCTGTTTT CCAAGTCCCA 790                810                830
CTTTGCGACT ACATGGTTGA GAAGGGTCTC AAGGATGTCA TTCAGAGTGT GCCCAGTGAT
GAAACGCTGA TGTACCAACT CTTCCCAGAG TTCCTACAGT AAGTCTCACA CGGGTCACTA 850                870                890
ACTGCCAATG TTTTGATCAA CAATGGTGAG GGCTCGGCTT AGATGCGCTT AGAGTTGCAT
TGACGGTTAC AAAACTAGTT GTTACCACTC CCGAGCCGAA TCTACGCGAA TCTCAACGTA 910                930                950
ACATAGCCCG ACATCGATGA TGGGATGTTG GGCGAATTAG TGTATATATT GCACAGTAGA
TGTATCGGGC TGTAGCTACT ACCCTACAAC CCGCTTAATC ACATATATAA CGTGTCATCT 970                990                1010
CATACAGAGT CGTTTTGATA ACGGCCGTTG CATTCAATTC ATCTTCTACT TGATTTAAAA
GTATGTCTCA GCAAAACTAT TGCCGGCAAC GTAAGTTAAG TAGAAGATGA ACTAAATTTT

AAAA
TTTT                            FIG. 2B
```

```
       -12         -10                                                       1
      Glu Phe Ile Glu Gln Asp Ala Val Val Thr Ile Ser Ala Thr Gln
      GAA TTC ATT GAA CAA GAC GCC GTT GTT ACC ATC TCC GCC ACC CAG

10
      Glu Asp Ala Pro Trp Gly Leu Ala Arg Ile Ser Ser Gln Glu Pro
      GAA GAC GCC CCA TGG GGT CTG GCC CGC ATC TCC AGC CAG GAA CCC 20                                          30
      Gly Gly Thr Thr Tyr Thr Tyr Asp Asp Ser Ala Gly Thr Gly Thr
      GGC GGC ACC ACT TAT ACC TAC GAT GAC TCT GCC GGT ACA GGC ACC

40
      Cys Ala Tyr Ile Ile Asp Thr Gly Ile Tyr Thr Asn His Thr Asp
      TGC GCA TAC ATC ATC GAC ACG GGC ATC TAC ACC AAC CAC ACT GAC 50                                          60
      Phe Gly Gly Arg Ala Lys Phe Leu Lys Asn Phe Ala Gly Asp Gly
      TTT GGC GGT CGT GCC AAG TTC CTC AAG AAC TTT GCC GGT GAC GGT

70
      Gln Asp Thr Asp Gly Asn Gly His Gly Thr His Val Ala Gly Thr
      CAA GAC ACC GAC GGC AAC GGT CAC GGC ACT CAC GTC GCC GGT ACC 80                                          90
      Val Gly Gly Thr Thr Tyr Gly Val Ala Lys Lys Thr Ser Leu Phe
      GTG GGC GGA ACA ACC TAT GGT GTA GCC AAG AAG ACA TCT CTC TTT

100
      Ala Val Lys Val Leu Asp Ala Asn Gly Gln Gly Ser Asn Ser Gly
      GCT GTC AAG GTC CTC GAC GCC AAC GGT CAG GGC TCC AAC TCC GGC 110                                         120
      Val Ile Ala Gly Met Asp Phe Val Thr Lys Asp Ala Ser Ser Gln
      GTC ATC GCA GGC ATG GAC TTT GTT ACC AAA GAC GCC TCG TCC CAA

130
      Asn Cys Pro Lys Gly Val Val Asn Met Ser Leu Gly Gly Pro
      AAC TGC CCC AAG GGC GTC GTA GTG AAC ATG TCG CTC GGT GGT CCC 140                                         150
      Ser Ser Ser Ala Val Asn Arg Ala Ala Ala Glu Ile Thr Ser Ala
      TCC TCC TCA GCC GTC AAC CGC GCC GCC GCC GAA ATC ACC AGC GCA

160
      Gly Leu Phe Leu Ala Val Ala Ala Gly Asn Glu Ala Thr Asp Ala
      GGC CTC TTC CTC GCT GTC GCA GCC GGC AAC GAA GCC ACT GAC GCC
```

FIG. 3A

```
             170                                              180
Ser Ser Ser Ser Pro Ala Ser Glu Glu Ser Ala Cys Thr Val Gly
TCC TCG TCG TCC CCT GCG TCC GAA GAA AGC GCC TGC ACT GTC GGC

190
Ala Thr Asp Lys Thr Asp Thr Leu Ala Glu Tyr Ser Asn Phe Gly
GCA ACC GAC AAG ACC GAC ACG CTG GCC GAG TAC TCC AAC TTT GGC 200                                              210
Ser Val Val Asp Leu Leu Ala Pro Gly Thr Asp Ile Lys Ser Thr
AGC GTC GTT GAC CTC CTT GCT CCC GGT ACG GAT ATC AAG TCT ACC

220
Trp Asn Asp Gly Arg Thr Lys Ile Ile Ser Gly Thr Ser Met Ala
TGG AAC GAC GGC CGC ACC AAG ATT ATT TCG GGC ACG TCC ATG GCT 230                                              240
Ser Pro His Val Ala Gly Leu Gly Ala Tyr Phe Leu Gly Leu Gly
AGC CCA CAT GTT GCT GGA CTG GGT GCG TAC TTT TTG GGC CTT GGA

250
Gln Lys Val Gln Gly Leu Cys Asp Tyr Met Val Glu Lys Gly Leu
CAA AAG GTT CAG GGT CTT TGC GAC TAC ATG GTT GAG AAG GGT CTC 260                                              270
Lys Asp Val Ile Gln Ser Val Pro Ser Asp Thr Ala Asn Val Leu
AAG GAT GTC ATT CAG AGT GTG CCC AGT GAT ACT GCC AAT GTT TTG
                                     281
Ile Asn Asn Gly Glu Gly Ser Ala AM
ATC AAC AAT GGT GAG GGC TCG GCT TAG ATGCGCTTAGAGTTGCATACATAG

CCCGACATCGATGATGGGATGTTGGGCGAATTAGTGTATATATTGCACAGTAGACATACA

GAGTCGTTTTGATAACGGCCGTTGCATTCAATTCATCTTCTACTTGATTTAAAAAAAA
```

```
          10                  30                  50
GGGGTTCATC ATCAACAGCC ATCGCAGCAA TACAAAAGCG TCTTCTCCAG CTCAACAACA
CCCCAAGTAG TAGTTGTCGG TAGCGTCGTT ATGTTTTCGC AGAAGAGGTC GAGTTGTTGT 70                  90                 110
CCTCTTGAAT AAGCCACGCT TTTTCATTCA CCGACGGTCA AAATGCGTCT TTCCATTCTT
GGAGAACTTA TTCGGTGCGA AAAAGTAAGT GGCTGCCAGT TTTACGCAGA AAGGTAAGAA 130                 150                 170
CTGGGTCTTC TTCCCCTCGC TCCTCGGCCT CCCGCCGTCG ACGCTGTTGA GCAGCGCTCC
GACCCAGAAG AAGGGGAGCG AGGAGCCGGA GGGCGGCAGC TGCGACAACT CGTCGCGAGG 190                 210                 230
GAGCCCGCTC CTCTTATTGA GGCCCAGGGC GAGATGATTG CCGACAAGTA CATTGTCAAG
CTCGGGCGAG GAGAATAACT CCGGGTCCCG CTCTACTAAC GGCTGTTCAT GTAACAGTTC 250                 270                 290
CTCAAGGAGG GTAGCGCTCT TGCTTCTCTC GATGCTGCCA TGGAGAAGCT TTCTGGCAAG
GAGTTCCTCC CATCGCGAGA ACGAAGAGAG CTACGACGGT ACCTCTTCGA AAGACCGTTC 310                 330                 350
GCCGACCACG TCTACAAGAA CATCTTCAAG GGCTTTGCTG CCTCTCTTGA CGAGAAGATG
CGGCTGGTGC AGATGTTCTT GTAGAAGTTC CCGAAACGAC GGAGAGAACT GCTCTTCTAC 370                 390                 410
GTTGAGGTCC TCCGCGCCCA CCCTGATGTC GAGTACATTG AGCAGGATGC TATCGTCAAC
CAACTCCAGG AGGCGCGGGT GGGACTACAG CTCATGTAAC TCGTCCTACG ATAGCAGTTG 430                 450                 470
ATCAACGCTG AGCAGCGCAA CGCTCCCTGG GGTCTTGCTC GCATCTCCAG CACCAGCCCC
TAGTTGCGAC TCGTCGCGTT GCGAGGGACC CCAGAACGAG CGTAGAGGTC GTGGTCGGGG 490                 510                 530
GGTACCTCCA CGTACAGATA CGACGACTCT GCCGGCCAGG GTACTTGCGT CTACGTCATC
CCATGGAGGT GCATGTCTAT GCTGCTGAGA CGGCCGGTCC CATGAACGCA GATGCAGTAG 550                 570                 590
GACACCGGTG TCGAGGCATC TCACCCCGAG TTTGAGGGCC GCGCCCAGAT GGTCAAGACG
CTGTGGCCAC AGCTCCGTAG AGTGGGGCTC AAACTCCCGG CGCGGGTCTA CCAGTTCTGC 610                 630                 650
TACTACGCCT CCAGCCGCGA TGGCAACGGC CACGGCACTC ACTGCGCCGG TACCATTGGC
ATGATGCGGA GGTCGGCGCT ACCGTTGCCG GTGCCGTGAG TGACGCGGCC ATGGTAACCG 670                 690                 710
TCCAGGACCT ACGGTGTCGC CAAGAAGACC CAGATCTTTG GTGTCAAGGT CCTCAACGAC
AGGTCCTGGA TGCCACAGCG GTTCTTCTGG GTCTAGAAAC CACAGTTCCA GGAGTTGCTG
```

FIG. 7A

```
           730                    750                    770
CAAGGCTCTG GCCAGTACTC CACCATCATC TCTGGTATGG ACTTTGTCGC CAACGACTAC
GTTCCGAGAC CGGTCATGAG GTGGTAGTAG AGACCATACC TGAAACAGCG GTTGCTGATG 790                    810                    830
CGCAACCGCA ACTGCCCCAA CGGTGTCGTT GCCTCCATGT CCATTGGTGG TGGCTACTCC
GCGTTGGCGT TGACGGGGTT GCCACAGCAA CGGAGGTACA GGTAACCACC ACCGATGAGG 850                    870                    890
TCTTCCGTGA ACAGCGCCGC TGCCAACCTC CAGCAATCTG GTGTCATGGT CGCCGTCGCT
AGAAGGCACT TGTCGCGGCG ACGGTTGGAG GTCGTTAGAC CACAGTACCA GCGGCAGCGA 910                    930                    950
GCTGGCAACA CAACGCTGA CGCTCGCAAC TACTCCCCTG CTTCTGAGTC CTCCATCTGC
CGACCGTTGT TGTTGCGACT GCGAGCGTTG ATGAGGGGAC GAAGACTCAG GAGGTAGACG 970                    990                   1010
ACTGTTGGTG CCACTGACCG CTACGACCGA CGATCCAGCT TCTCCAACTA CGGCAGCGTT
TGACAACCAC GGTGACTGGC GATGCTGGCT GCTAGGTCGA AGAGGTTGAT GCCGTCGCAA 1030                   1050                   1070
TTGGACATCT TTGCCCCCGG TACCGACATT CTCTCCACCT GGATCGGCGG CAGCACCAGA
AACCTGTAGA AACGGGGCC ATGGCTGTAA GAGAGGTGGA CCTAGCCGCC GTCGTGGTCT 1090                   1110                   1130
TCCATCTCTG GTACCTCCAT GGCTACTCCC CACGTTGCTG GTCTCGCTGC CTACCTTATG
AGGTAGAGAC CATGGAGGTA CCGATGAGGG GTGCAACGAC CAGAGCGACG GATGGAATAC 1150                   1170                   1190
ACTCTCGGAC GCGCCACCGC CAGCAACGCT TGCCGATACA TTGCCCAGAC TGCCAACCAG
TGAGAGCCTG CGCGGTGGCG GTCGTTGCGA ACGGCTATGT AACGGGTCTG ACGGTTGGTC 1210                   1230                   1250
GGCGATCTGA GCAACATTTC CTTCGGCACT GTCAACCTGC TTGCCTACAA CAACTACCAG
CCGCTAGACT CGTTGTAAAG GAAGCCGTGA CAGTTGGACG AACGGATGTT GTTGATGGTC 1270                   1290                   1310
GGCTAAGTGC TTCAGTCAGC TCTAAAAGTT GGAAGATATG AAACGAGATT TGAATGCATC
CCGATTCACG AAGTCAGTCG AGATTTTCAA CCTTCTATAC TTTGCTCTAA ACTTACGTAG 1330                   1350                   1370
TGTACATAGA TGAGCACATT CATATCGGTC TTACGACCAT ATTTAGTCAT ATTTAAAAAT
ACATGTATCT ACTCGTGTAA GTATAGCCAG AATGCTGGTA TAAATCAGTA TAAATTTTA

AAA
TTT             FIG. 7B
```

```
GGGGTTCATCATCAACAGCCATCGCAGCAATACAAAAGCGTCTTCTCCAGCTCAACAAC
```

```
                                                        -108
                                                        Met Arg Leu Ser
ACCTCTTGAATAAGCCACGCTTTTTCATTCACCGACGGTCAAA ATG CGT CTT TCC
```

|  | | | | -100 | | | | | | | | -90 |
|---|---|---|---|---|---|---|---|---|---|---|---|---|
| Ile | Leu | Leu | Gly | Leu | Leu | Pro | Leu | Ala | Pro | Arg | Pro | Pro | Ala | Val |
| ATT | CTT | CTG | GGT | CTT | CTT | CCC | CTC | GCT | CCT | CGG | CCT | CCC | GCC | GTC |

```
                           -80
Asp Ala Val Glu Gln Arg Ser Glu Pro Ala Pro Leu Ile Glu Ala
GAC GCT GTT GAG CAG CGC TCC GAG CCC GCT CCT CTT ATT GAG GCC

-70                                              -60
Gln Gly Glu Met Ile Ala Asp Lys Tyr Ile Val Lys Leu Lys Glu
CAG GGC GAG ATG ATT GCC GAC AAG TAC ATT GTC AAG CTC AAG GAG

-50
Gly Ser Ala Leu Ala Ser Leu Asp Ala Ala Met Glu Lys Leu Ser
GGT AGC GCT CTT GCT TCT CTC GAT GCT GCC ATG GAG AAG CTT TCT

-40                                              -30
Gly Lys Ala Asp His Val Tyr Lys Asn Ile Phe Lys Gly Phe Ala
GGC AAG GCC GAC CAC GTC TAC AAG AAC ATC TTC AAG GGC TTT GCT

-20
Ala Ser Leu Asp Glu Lys Met Val Glu Val Leu Arg Ala His Pro
GCC TCT CTT GAC GAG AAG ATG GTT GAG GTC CTC CGC GCC CAC CCT

-10                                               1
Asp Val Glu Tyr Ile Glu Gln Asp Ala Ile Val Asn Ile Asn Ala
GAT GTC GAG TAC ATT GAG CAG GAT GCT ATC GTC AAC ATC AAC GCT

10
Glu Gln Arg Asn Ala Pro Trp Gly Leu Ala Arg Ile Ser Ser Thr
GAG CAG CGC AAC GCT CCC TGG GGT CTT GCT CGC ATC TCC AGC ACC 20                                              30
Ser Pro Gly Thr Ser Thr Tyr Arg Tyr Asp Asp Ser Ala Gly Gln
AGC CCC GGT ACC TCC ACG TAC AGA TAC GAC GAC TCT GCC GGC CAG

40
Gly Thr Cys Val Tyr Val Ile Asp Thr Gly Val Glu Ala Ser His
GGT ACT TGC GTC TAC GTC ATC GAC ACC GGT GTC GAG GCA TCT CAC 50                                              60
Pro Glu Phe Glu Gly Arg Ala Gln Met Val Lys Thr Tyr Tyr Ala
CCC GAG TTT GAG GGC CGC GCC CAG ATG GTC AAG ACG TAC TAC GCC
```

FIG. 8A

```
                                        70
Ser Ser Arg Asp Gly Asn Gly His Gly Thr His Cys Ala Gly Thr
TCC AGC CGC GAT GGC AAC GGC CAC GGC ACT CAC TGC GCC GGT ACC 80                                      90
Ile Gly Ser Arg Thr Tyr Gly Val Ala Lys Lys Thr Gln Ile Phe
ATT GGC TCC AGG ACC TAC GGT GTC GCC AAG AAG ACC CAG ATC TTT

100
Gly Val Lys Val Leu Asn Asp Gln Gly Ser Gly Gln Tyr Ser Thr
GGT GTC AAG GTC CTC AAC GAC CAA GGC TCT GGC CAG TAC TCC ACC 110                                     120
Ile Ile Ser Gly Met Asp Phe Val Ala Asn Asp Tyr Arg Asn Arg
ATC ATC TCT GGT ATG GAC TTT GTC GCC AAC GAC TAC CGC AAC CGC

130
Asn Cys Pro Asn Gly Val Val Ala Ser Met Ser Ile Gly Gly Gly
AAC TGC CCC AAC GGT GTC GTT GCC TCC ATG TCC ATT GGT GGT GGC 140                                     150
Tyr Ser Ser Ser Val Asn Ser Ala Ala Ala Asn Leu Gln Gln Ser
TAC TCC TCT TCC GTG AAC AGC GCC GCT GCC AAC CTC CAG CAA TCT

160
Gly Val Met Val Ala Val Ala Ala Gly Asn Asn Asn Ala Asp Ala
GGT GTC ATG GTC GCC GTC GCT GCT GGC AAC AAC AAC GCT GAC GCT 170                                     180
Arg Asn Tyr Ser Pro Ala Ser Glu Ser Ser Ile Cys Thr Val Gly
CGC AAC TAC TCC CCT GCT TCT GAG TCC TCC ATC TGC ACT GTT GGT

190
Ala Thr Asp Arg Tyr Asp Arg Arg Ser Ser Phe Ser Asn Tyr Gly
GCC ACT GAC CGC TAC GAC CGA CGA TCC AGC TTC TCC AAC TAC GGC 200                                     210
Ser Val Leu Asp Ile Phe Ala Pro Gly Thr Asp Ile Leu Ser Thr
AGC GTT TTG GAC ATC TTT GCC CCC GGT ACC GAC ATT CTC TCC ACC

220
Trp Ile Gly Gly Ser Thr Arg Ser Ile Ser Gly Thr Ser Met Ala
TGG ATC GGC GGC AGC ACC AGA TCC ATC TCT GGT ACC TCC ATG GCT 230                                     240
Thr Pro His Val Ala Gly Leu Ala Ala Tyr Leu Met Thr Leu Gly
ACT CCC CAC GTT GCT GGT CTC GCT GCC TAC CTT ATG ACT CTC GGA
```

FIG. 8B

```
                                          250
Arg Ala Thr Ala Ser Asn Ala Cys Arg Tyr Ile Ala Gln Thr Ala
CGC GCC ACC GCC AGC AAC GCT TGC CGA TAC ATT GCC CAG ACT GCC 260                                           270
Asn Gln Gly Asp Leu Ser Asn Ile Ser Phe Gly Thr Val Asn Leu
AAC CAG GGC GAT CTG AGC AAC ATT TCC TTC GGC ACT GTC AAC CTG

279
Leu Ala Tyr Asn Asn Tyr Gln Gly OC
CTT GCC TAC AAC AAC TAC CAG GGC TAA GTGCTTCAGTCAGCTCTAAAAGTT

GGAAGATATGAAACGAGATTTGAATGCATCTGTACATAGATGAGCACATTCATATCGGTC

TTACGACCATATTTAGTCATATTTAAAAATAAA
```

PROTEOLYTIC ENZYMES

This is a continuation of copending application Ser. No. 07/696,337 filed on May 1, 1919, now abandoned, which is a continuation of Ser. No. 07/035,846 filed on Apr. 3, 1987, now abondoned.

BACKGROUND

This invention relates to novel serine proteases isolated from a culture medium of the fungus *Tritirachium album*. The serine proteases of the present invention have a high degree of stability in aqueous solutions and dry detergent formulations. The invention further relates to detergent compositions containing such proteases and to the use of the proteases in detergents and cleaners or spot cleaners. In addition, the present invention further relates to DNA sequences encoding for the proteases and to a method for producing the proteases.

Serine proteases are proteolytic enzymes having a serine residue at their active site. Modification of the active site serine residue by agents such as phenylmethylsulfonylfluoride (PMSF) inactivates these enzymes. There are two classes of serine proteases, chymotrypsin-like proteases and subtilisin-like proteases. Subtilisins are serine proteases which generally act to cleave internal peptide bonds of proteins or peptides. Subtilisins are secreted by a number of *Bacillus* species and extensively used commercially (see U.S. Pat. No. 3,623,957, J. Miller, 1970, *J. Appl. Bacteriol*, 33, 207; Ward, O. P. 1983, pp. 251-317, *Enzymes and Biotechnology*, ed., W. M. Fogarty, Applied Science Publishers, London). Subtilisins have been utilized in a number of detergent formulations (see U.S. Pat. Nos. 1,240,058, 3,749,671; 3,790,482; 4,266,031, U.K. Patent No. 1315937).

The use of proteases in industrial processes which require hydrolysis of protein has been limited due to the enzyme instability under the temperature and pH conditions associated with such processes. Although thermal inactivation of the protease may be the most important factor in restricting the industrial use of a protease, other factors such as lack of effectiveness over broad pH ranges and use of denaturing agents in detergent formulations may also have a detrimental effect regarding the use of proteases in industrial processes. The known Bacillus derived subtilisins are not ideal for all applications as detergent enzymes, in particular, application requiring greater storage stability and activity at broader ranges of pH and temperature. Therefore there is a need for a class of proteases that are characterized by high stability with respect to temperature, pH, denaturing agents and the like.

There also is a need for proteases that are compatible with detergents and have sufficient shelf-life in liquid detergent formulations to be commercially practical. Thermostable fungal serine proteases have been evaluated in detergent applications, including proteases obtained from *Tritirachium album* (Ebeling, W. et al., 1971, German Offenbach, 1965, 281), *Malbranchea pulchella* (Ong, P.S. et al., Can. J. Microbiol. 22, 165), *Acremonium kiliense, Fusarium* and *Gibberella* spp (Isono, M., et al., 1972, U.S. Pat. No. 3652399). Proteinase K (EC 3, 4, 21, 14) was isolated from *Tritirachium album* (Ebeling, W. et al., 1974, Eur. J. Biochem. 47, 91-97) and has been extensively studied by different groups (Kraus, E. et al., 1976, Hoppe Seyler's Z. Physiol. Chem. 357, 937-947, ibid. 357, 233-237, and Morihara, K. et al., 1975, Agr. Biol. Chem. 39, 1489-1492). The three dimensional structure of proteinase K is similar to that of subtilisins (Paehler, A. et al., 1983, EMBO J. 3, 1311-1314) and there is about 35% homology of the amino acid sequence of proteinase K with that of subtilisins. (Jany, K-D., et al., FEBS Letters, 199, 139-144). Detergent compatibility of proteinase K has been suggested from its activity in the presence of high concentration of detergents (Hilz, H. et al., 1975, Eur. J., Biochem., 56, 103-108).

Proteolytic enzymes generally catalyze the cleavage of peptide bonds only within a certain range of pH and temperature. Moreover, even under optimal conditions, a proteolytic enzyme retains its activity only when its polypeptide chain is in native conformation. Unfolding of the native structure often occurs when the enzyme is exposed to extremes of pH or temperature or to certain detergent additives such as surfactants and metal-chelating agents. The latter exert their effect especially on enzymes that require metal ions such as $Ca^{2+}$ for stabilizing their native structure, i.e., bacterial subtilisin. For proteases, partial unfolding of the native conformation of the enzyme may lead to acceleration of autodigestion and therefore, to irreversible enzyme inactivation. Because most commercial laundry detergents have an alkaline pH, it is desirable that the enzyme utilized in such detergents be active and stable in a pH range of between 7.5 and 13 and in a temperature range of between 20°-65° C. Moreover, it is desirable that the activity of such enzymes be relatively independent of calcium and magnesium ions and be compatible with surfactants and sequestrant builders. Bacterial serine proteases of the subtilisin family fulfill these requirements to some extent, however their stability in liquid detergent formulation is limited.

SUMMARY OF THE INVENTION

The present invention relates to novel serine proteases that are characterized by improved stability in detergent formulations. In particular, the present invention describes the isolation, purification and characterization of novel serine proteases obtained from the strain of fungus *Tritirachium album* Limber (ATCC 22563). The serine proteases of the present invention have been found to be superior detergent enzymes and possess a high degree of thermal stability in aqueous solutions particularly at elevated temperatures, thereby making the proteases suitable for use as additives in commercial liquid detergent formulations. The present invention further relates to the isolation and characterization of the genes encoding such proteases. The invention further relates to the use of the serine proteases of the present invention in detergents and cleaners or spot cleaners and compositions containing the serine proteases.

In addition, the present invention relates to the use of an oligonucleotide probe which hybridizes with complementary DNA sequences in the genomic or cDNA clones of the serine proteases disclosed herein. Finally the present invention relates to DNA sequences useful in securing expression in a procaryotic or eucaryotic host cell a serine protease isolated from culture media containing strain of *T. album* Limber (ATCC 22563) and the method for isolating such proteases.

The present invention further relates to a purified and isolated serine protease having the structural conformation (i.e., continuous sequence of amino acid residues) of a serine protease isolated from a culture of *Tritirachium*

*album* Limber strain ATCC 22563 and characterized by being the product of procaryotic or eucaryotic expression of an exogenous DNA sequence.

Also, the present invention provides a process for the production of a serine protease having the structural conformation of a serine protease isolated from a culture or *Tritirachium album* Limber strain ATCC 22563, said process comprising growing under suitable nutrient condition procaryotic or eucaryotic host cells transformed or transfected with a DNA vector including a DNA sequence useful in securing expression in a procaryotic or eucaryotic host cell the desired serine protease and isolating desired serine protease of the expression of DNA sequences in said vector.

Also provided herein are oligonucleotide probes capable of hybridizing with a DNA sequence capable of expressing in a procaryotic or eucaryotic host cell a serine protease having the structural conformation of a serine protease isolated from culture of media of *Tritirachium album* Limber strain ATCC 22563.

BRIEF DESCRIPTION OF THE DRAWINGS

FIG. 1(A–B) represents the nucleotide sequence of the genomic clone for protease TW7;

FIG. 2(A–B) represents the nucleotide sequence of the cDNA clone for protease TW7;

FIG. 3(A–B) represents the nucleotide sequence of the coding strand, correlated with the amino acid sequence of the protease TW7;

Figure 4A:
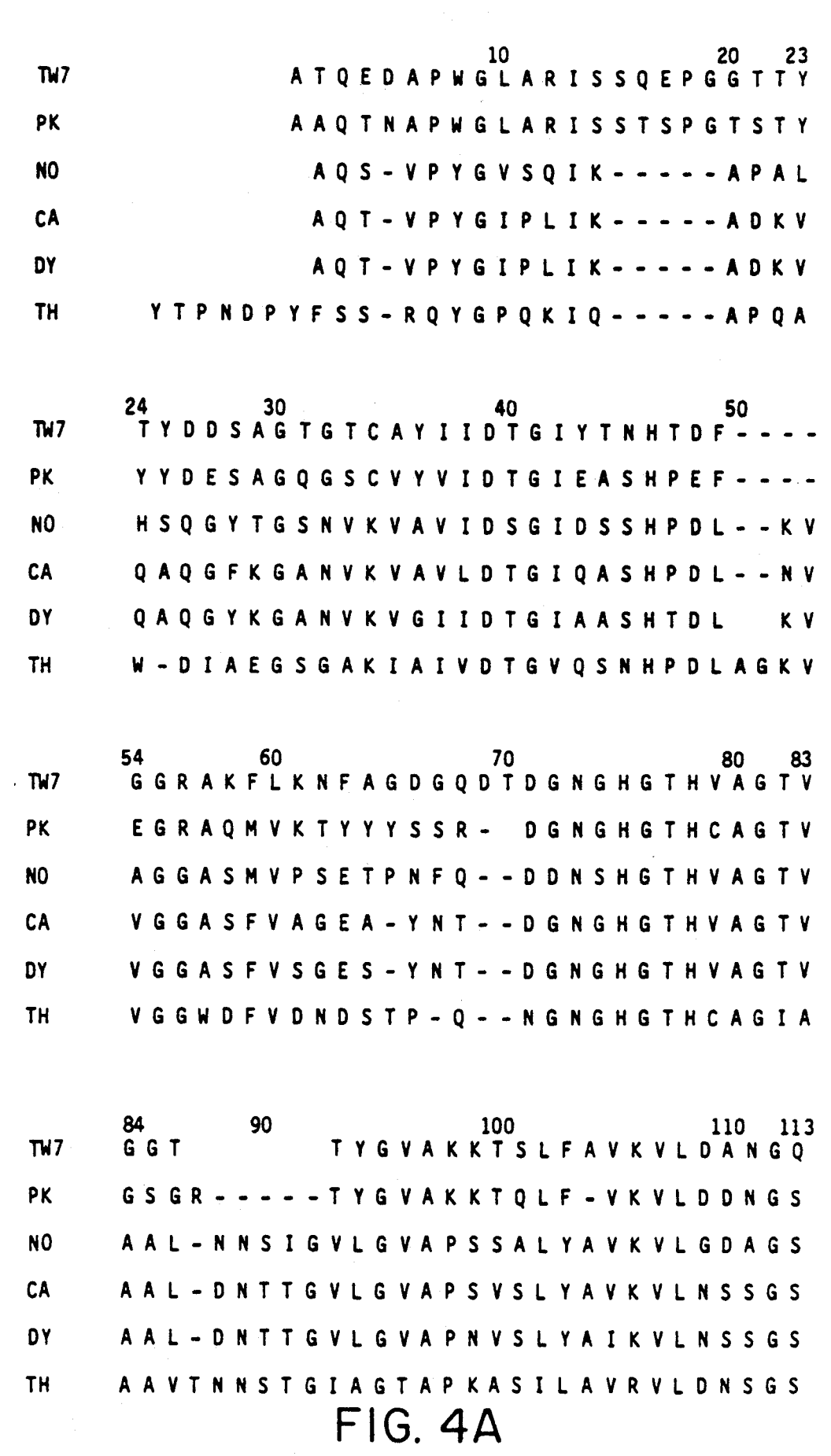
Figure 4B:
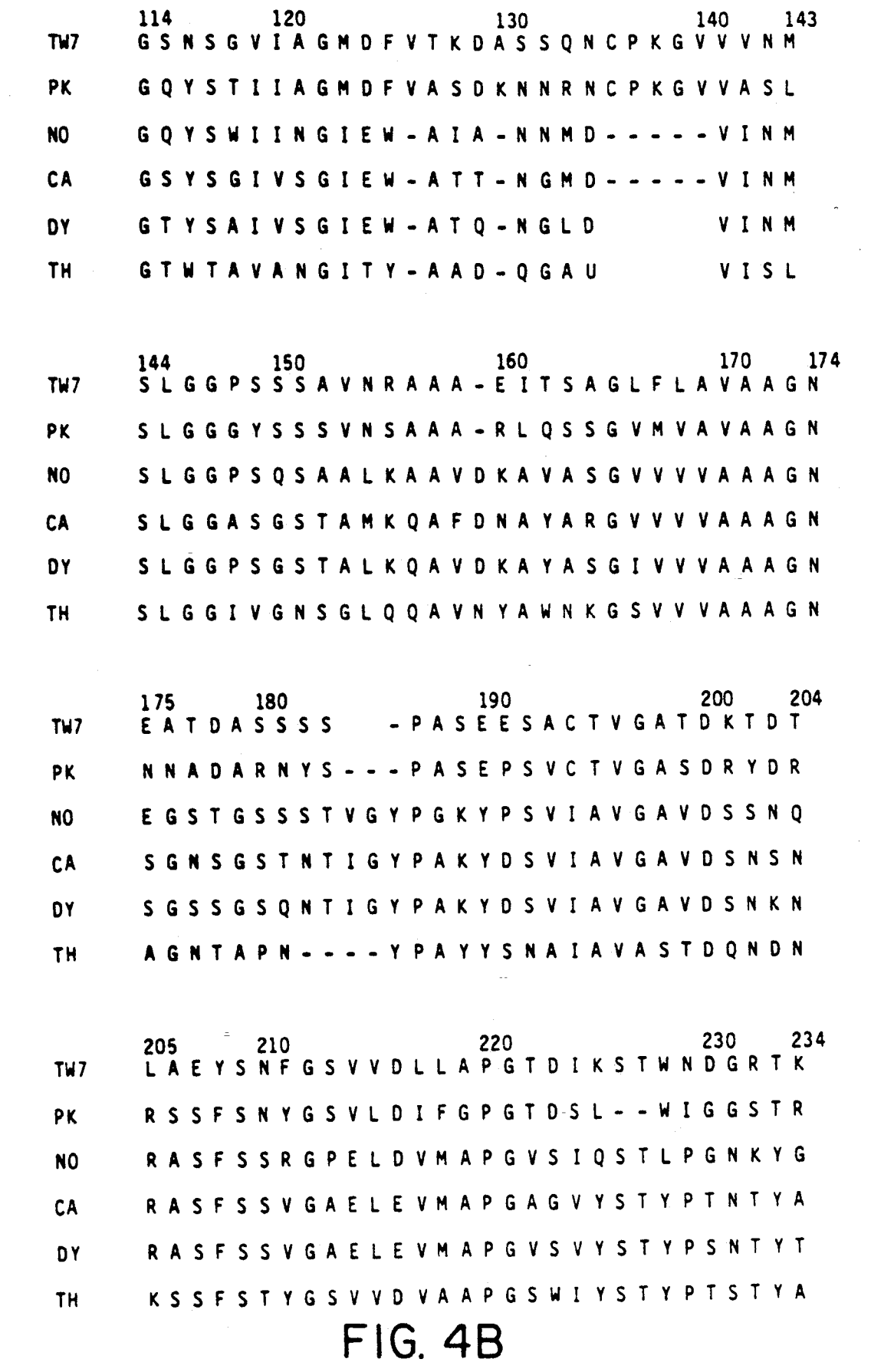
Figure 4C:
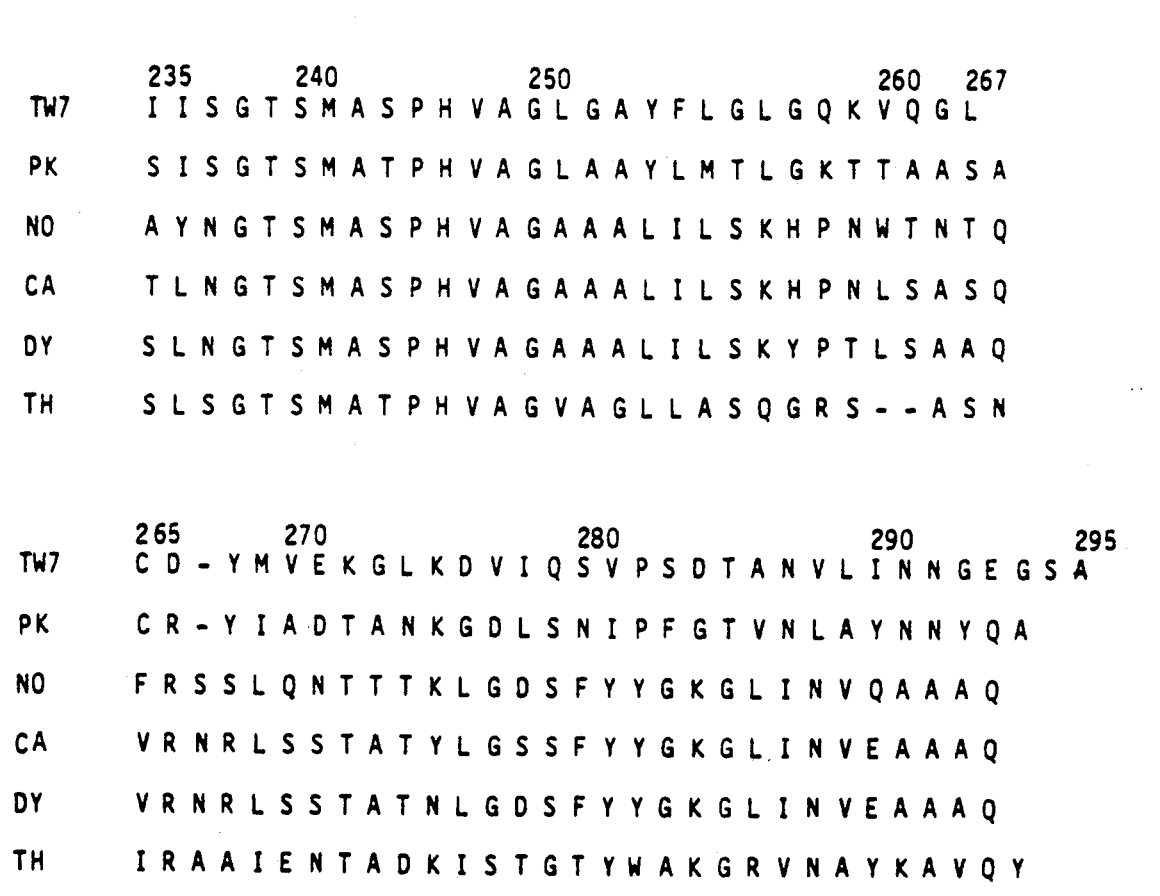

FIG. 4(A–C) represents a comparison of the amino acid sequences of protease TW7 with those of proteinase K, subtilisin novo, subtilisin Carlsberg, subtilisin DY and thermitase;

FIG. 7(A–B) represents the nucleotide sequence of the cDNA clone for protease TW3;

FIG. 8(A–C) represents the nucleotide sequence of the coding strand, correlated with the amino acid sequence of the protease TW3;

FIG. 9(A–C) represents a comparison of the amino acid sequences of protease TW3 with those of proteinase K, subtilisin novo, subtilisin Carlsberg, subtilisin DY and thermitase;

FIG.1(A–B) represents a flow diagram illustrating the components utilized in construction of pCFM 1156 TW7.

DETAILED DESCRIPTION

Figure 5:
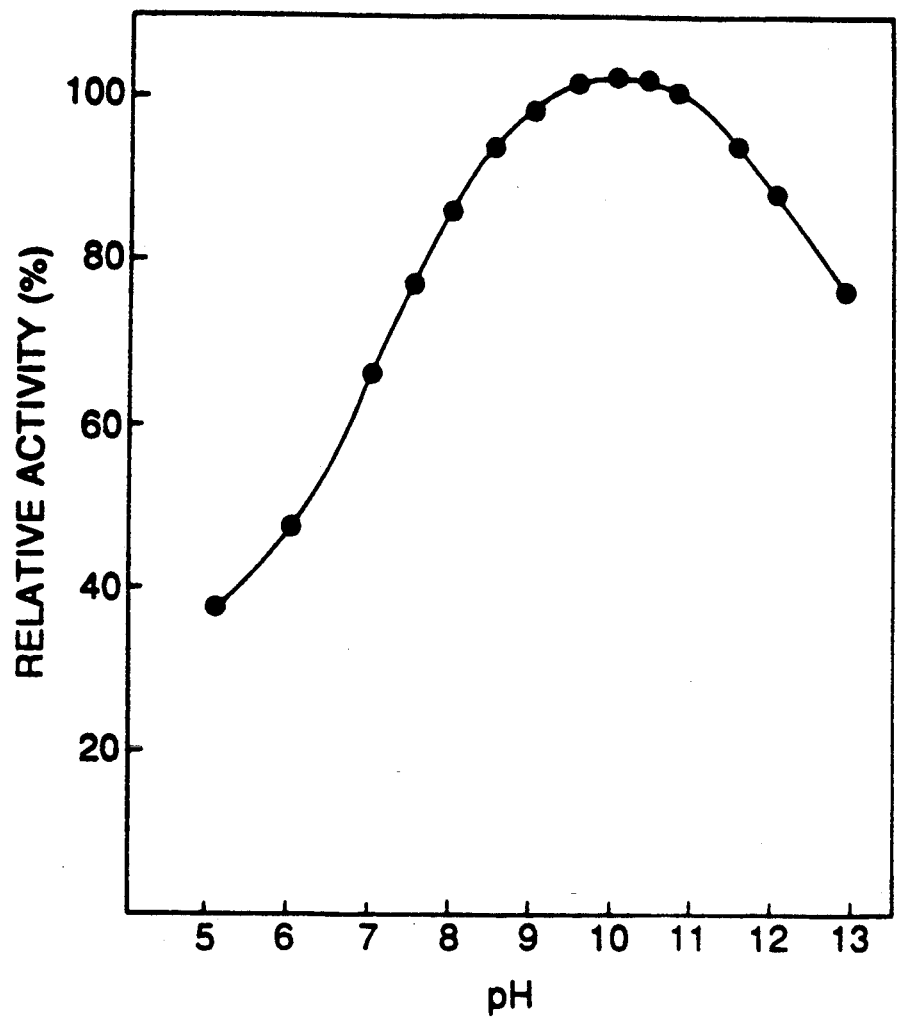
FIG. 5 represents the pH profiles of protease TW7.

Because *T. album* Limber is a slow growing fungus capable of producing only low level quantities of proteases, production of proteinase K or any other subtilisin-like enzymes in large commercial quantities by fermenting the fungus, is not practical. In addition, the growth of the fungus *T. album* as well as the production of proteases are slow, making the commercialization of a subtilisin-like enzyme uneconomical.

One aspect of the present invention relates to the isolation of a gene encoding the novel serine proteases of the present invention from *T. album* Limber, and the cloning and expression of such a gene in a suitable microorganism. The gene was isolated using a deoxyribonucleotide oligomer that hybridizes with a gene having a DNA sequence encoding the amino acid residues around the active serine residue. Using this approach, more than one gene has been isolated from the genomic library. This suggests the production of more than one serine protease from *T. album* Limber. The amino acid sequences of the amino termini of the proteases were found to be different. The novel proteases, protease TW7 and protease TW3 were isolated and characterized.

The gene encoding for protease TW7 was isolated from a genomic library. In particular, the isolation of subtilisin-like genes from the genomic library of *T. album* comprises (1) construction of a library from the genomic DNA of *T. album* Limber in a pBR322 plasmid; (2) screening of the genomic library with a labeled oligonucleotide probe which hybridizes specifically with subtilisin-like genes; (3) restriction enzyme analysis of positive clones followed by Southern blot hybridization with various restriction fragments for the identification of clones carrying the entire gene; (4) subcloning of restrictive fragments carrying the entire gene in bacteriophage M13 for DNA sequence analysis; (5) designing oligonucleotide primers based on partial DNA sequence data to complete DNA sequencing of both strands of the gene.

Sequencing of both strands of the genomic gene revealed the presence of two introns. In order to express genes containing introns in microorganisms that lack splicing enzymes, e.g., *B. subtilis, E. coli*, etc., it is necessary to reconstruct the gene (i.e., utilizing in vitro splicing) or obtain the gene from a cDNA library. The genes encoding for protease TW7 and protease TW3 were isolated from a cDNA library. The isolation of subtilisin genes from the cDNA library of *T. album* Limber comprises (1) isolating of total RNA from *T. album* Limber; (2) fractioning of RNA on an oligonucleotide dT cellulose column and isolation of polyadenylated mRNA fraction; (3) using an oligonucleotide probe for Northern blot analysis to confirm the presence of subtilisin-like mRNA; (4) cDNA synthesis and construction of a cDNA library in a pBR322 derived plasmid; (5) screening of the cDNA library with a $^{32}$P-labeled oligonucleotide probe that was utilized in Step 3; (6) isolation and restriction analysis of positive cDNA clones; (7) subcloning of restriction fragments from positive cDNA clones that carry the entire protein coding sequence in bacteriophage M13 for DNA sequencing; (8) using oligonucleotide primers to complete the DNA sequencing of both strands of the gene.

In accordance with the above procedures, two cDNA genes have been identified whose amino acid sequences as deduced from the DNA sequences indicated that their products are subtilisin-like enzymes. One of the gene products has the amino acid sequence represented in FIG. 3 and was named protease TW7. Protease TW7 exhibits approximately 53% amino acid sequence homology with proteinase K from *T. album* Limber. The putative amino acid sequence of protease TW7 indicated that unlike proteinase K, this protease has a net negative charge and therefore may be separated from the other proteases using DEAE sepharose or DEAE-cellulose chromatography. The second of putative gene products was named protease TW3. The degree of amino acid sequence homology of this protease and proteinase K from *T. album* Limber was approximately 90%. The putative amino acid sequence of protease TW3 indicated that the enzyme has a net positive charge and therefore can be separated from the other proteases by CM-cellulose chromatography.

The serine proteases of the present invention were isolated from the culture broth of *T. album* Limber strain (CBS 348.55) ATCC Deposit No. 22563 as follows:

The particular fungus *T. album* strain (ATCC 22563) was grown in media containing only proteins as nitrogen sources, e.g., skim milk, bovine serum albumin or soy flour. The culture media were tested for proteolytic activity using azocasein as the substrate. When the proteolytic activity reached a plateau or started to decline, the culture broth was separated from fungal mycelia by centrifugation. Proteins in the supernatant were precipitated using ammonium sulfate. The precipitate was dissolved in 20 mM sodium phosphate buffer at pH 6.0 and the solution was dialyzed against the same buffer. The solution was passed through a column of CM-52 (Whatman) to capture proteinase K-like enzymes and then passed through a DE-52 (Whatman) column. Proteinase TW7 was eluted from the DE-52 column with 100 mM NaCl in 20 mM sodium phosphate at pH 6.0. It was dialyzed against water and then lyophilized. Protease TW3 was bound to CM-52 from which it was eluted with 200 mM NaCl in 20 mM sodium phosphate at pH 6.0.

Figure 6:
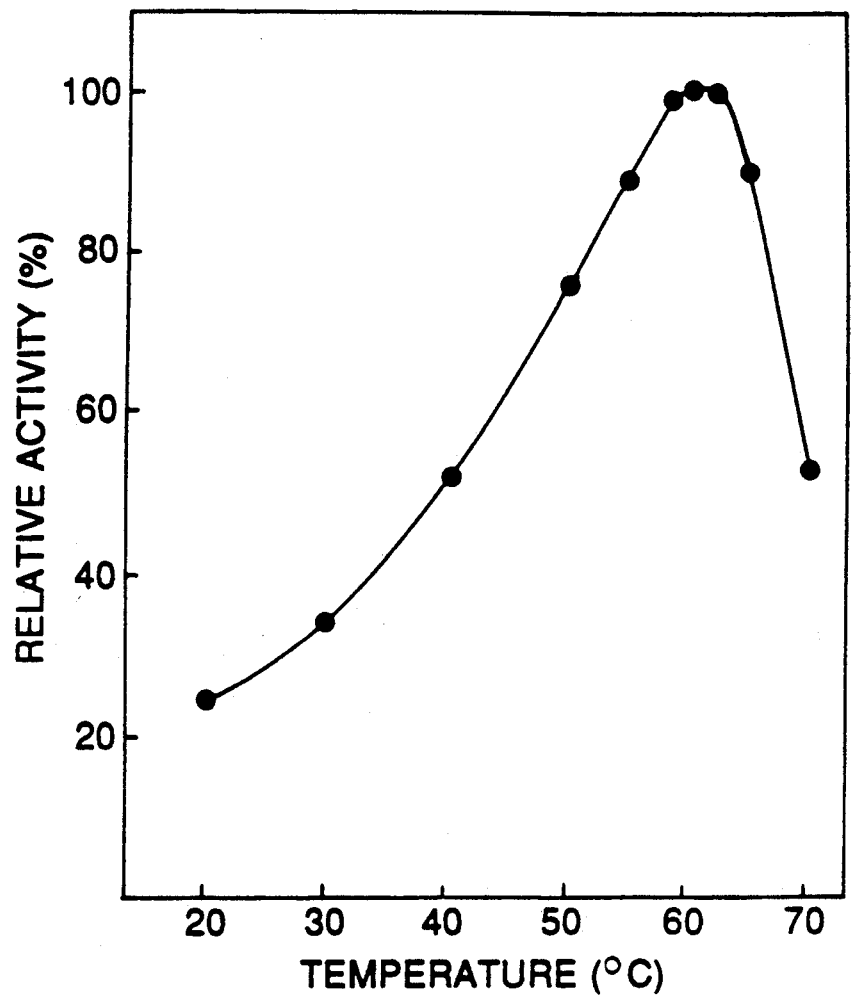
FIG. 6 represents the temperature profiles of the protease TW7.
Figure 10:
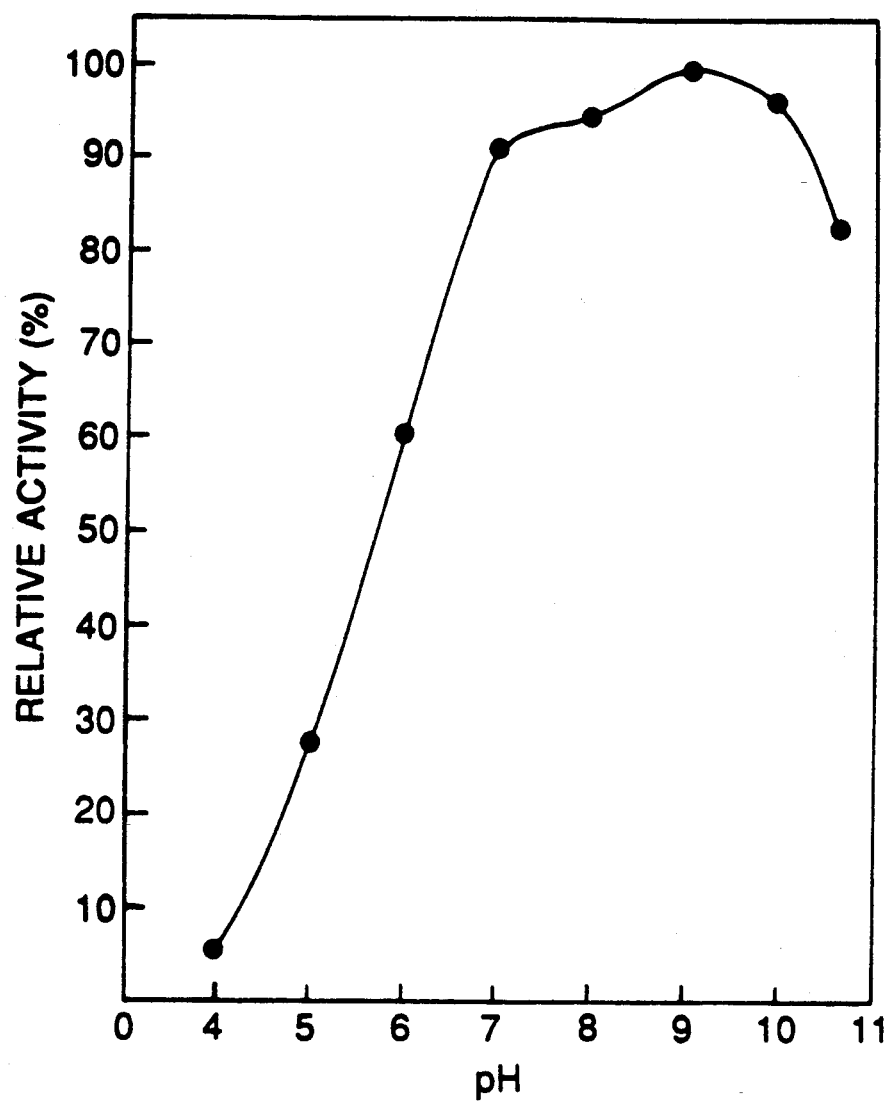
FIG. 10 represents the pH profiles of protease TW3.

The detergent compatibility properties of the serine proteases of the present invention have been characterized. As shown in FIGS. 5 and 10, protease TW7 and protease TW3 are active over a wide pH range. Although the maximum activity occurs approximately at pH 10, protease TW7 has considerable activity within pH range 9 to 13. In addition, protease TW7 retains at least 45% of its maximum activity present in a buffer having pH of 6.0. As represented in FIG. 6, protease TW7 has enzymatic activity over a broad temperature range. The maximum activity is between 60°-65° C., although at 20° C. protease TW7 retains at least 25% of its original activity. Protease TW7 is stable at 52° C. in buffers of various pH values. Following incubation for a period of one hour at pH 8 and 10.3, approximately 100% of the original activity is retained, while under similar conditions a commercial subtilisin retained only up to 30% of its original activity. In the presence of 0.5% SDS at pH 8.0, protease TW7 retains 100% of its activity after one hour incubation at 52° C. while the commercial subtilisin retains only about 5-6% of its original activity.

Figure 11:
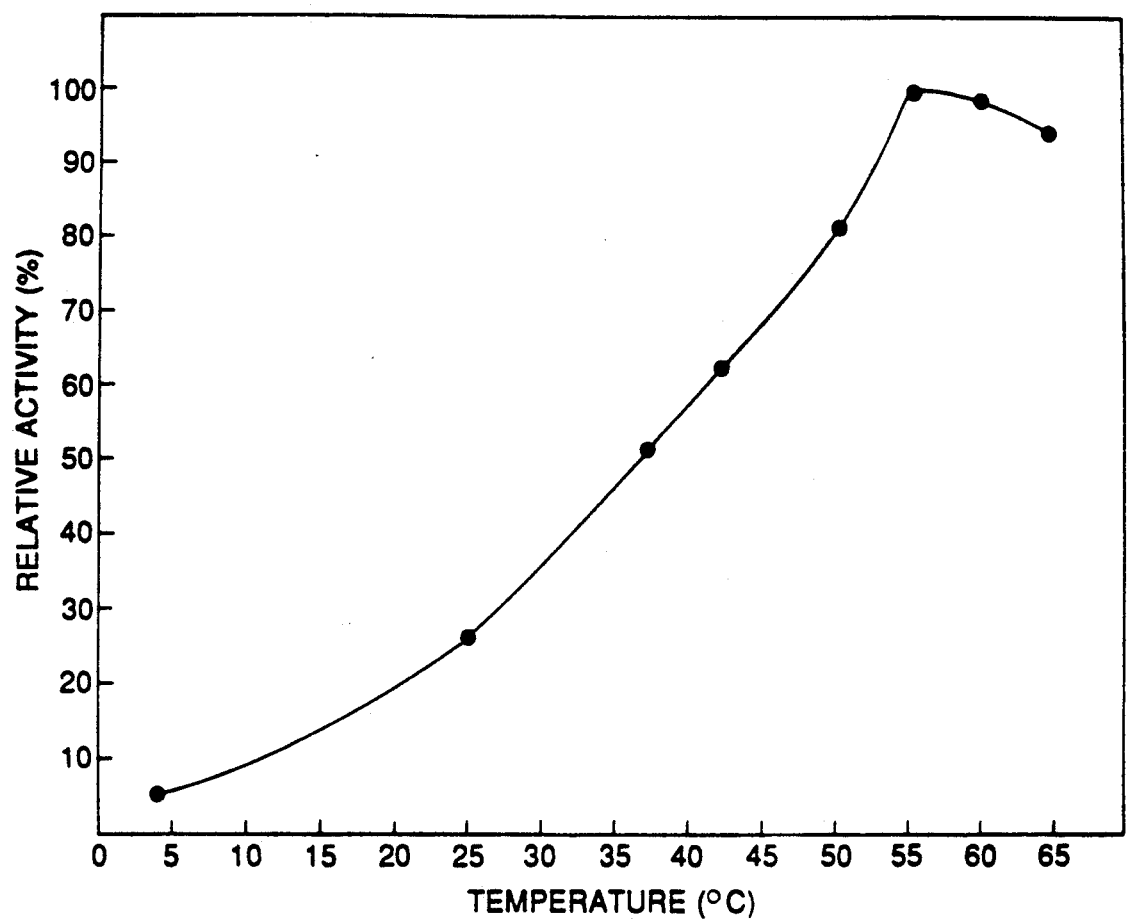
FIG. 11 represents the temperature profiles of the protease TW3.

As illustrated in FIG. 10, protease TW3 is also active over a broad pH range. For example, protease TW3 has its highest enzymatic activity at pH 9, although there is considerable activity within a pH range of from 7 to 10. As represented in FIG. 11, the temperature range of enzymatic activity of protease TW3 is also broad. The maximum activity is between 55°-65° C., although at 25° C., protease TW3 retains at least 32% of its activity. This enables protease TW3 to be active at a wide range of washing temperature. In addition, protease TW3 is very stable at 50° C. in buffers of various pH values. Following one hour incubation at pH 4.0, 8 and 10.0, 50-90% of the original activity of protease TW3 is retained, while under similar conditions a commercial subtilisin retains only minimal activity.

The stability of the serine proteases of the present invention have been evaluated in different laundry detergent formulations. Any endogenous enzyme that was present was inactivated prior to evaluation by heating the detergent formulation at 65° C. for one hour.

In addition to the enzyme the commercial washing powder composition of the present invention will generally contain:

(a) At least one surfactant which may be anionic, non-ionic, or amphoteric, or a water-soluble soap. Typically, an anionic surfactant (e.g. a linear alkyl aryl sulphonate) is used in admixture with a non-ionic (e.g. an alkyl phenyl polyglycol ether) in amounts of 5-30 and 1-5 percent by weight, respectively, of the washing composition.

(b) One or more builders, preferably having a concomitant sequestering function. Sodium tripolyphosphate, sodium citrate, sodium silicate, and zeolites are examples of such compounds, usually constituting from 10 to 70 percent by weight of the detergent composition.

(c) A bleaching agent, preferably a peroxy compound such as sodium perborate, typically incorporated in an amount up to 30 percent by weight of the composition.

(d) Ancillary agents, such as carboxymethyl cellulose, optical brighteners and perfumes. If required, a pH-adjusting agent is added to give a pH of the laundering medium in the range of from 8.0 to 10.5.

The particulate protease preparation of the invention is added in an amount calculated to give a protease activity of at least 0.1 Anson units (AU, vide infra), preferably 0.5-2.5 AU per 100 g of washing composition. If required, balance to 100 percent may be established with an inorganic filler, preferably sodium sulphate.

Liquid detergent compositions may be prepared from enzyme slurries, preferably in non-aqueous media. Typically, such slurries may consist of a suspension of finely ground protease concentrate in a liquid non-ionic surfactant, for example Tergitol 15 S 9 or a mixture of such surfactants. Usually, the slurry will also contain one or more inorganic fillers, such as finely ground sodium chloride, optionally in admixture with a suspension stabilizer, for example fumed silica (Aerosil 200). Tergitol and Aerosil are trade marks.

The protease slurry of the invention is added in an amount calculated to give a protease activity of at least 0.1 AU preferably 0.5-2.5 AU per 100 g of liquid detergent composition.

The washing compositions may be prepared in the usual manner, for example by mixing together the components. Alternatively, a pre-mix is made, which is then mixed with the remaining ingredients.

The following Examples will further serve to illustrate the invention although it will be understood that the invention is not limited to these specific examples.

Because of the good stability and activity properties described, the proteolytic enzyme according to the invention can be used in all fields where proteolytic enzymes are generally used. In particular, it can be used for detergents and cleansers or spot removers, as a depilatory in tanning, and also in the food industry for the preparation of protein hydrolysates and in serology for the detection of incomplete antibodies. It is particularly advantageous for use in the food industry and in serology that the enzyme according to the invention has such an excellent stability in the solid or dissolved form that physiologically acceptable quantities of calcium ions may not be necessary to stabilize the enzyme in aqueous solutions, in contrast to those of other enzyme preparations.

EXAMPLE 1

Production of Serine Protease from *Tritirachium album* Limber

The fungus, *Tritirachium album* Limber (CBS348.55, ATCC 22563) was obtained from American Type Culture Collection, 912301 Parklawn Dr., Rockville, MD. The fungus belongs to the family Moniliaceae (Limber, 1940, Mycologia, 32,23–30). Typical features of the fungus include hyaline mycelium, sparingly branched hyaline conidia, pure white dense mycelliar mat forming low dome or hemisphere. According to the Centralbureau voor Schimmelcultures (Oosterstraat 1, Baarn, P. O. Box 273, 3740 Ag Baarn, Netherland, ref. MAAS/tvs/714, dated Oct. 4, 1985) the strain was originally isolated from deceased skin. This strain is not the same strain (CBS 747.69) from which proteinase K was isolated. *Tritirachium album* was propagated on malt-peptone-agar plates that contained 3% malt extract, 0.3% casein peptone and 2% bactoagar. The fungus was allowed to sporulate at room temperature for 7–8 days. Spores were collected in 15–20 ml of sterile distilled water and were maintained at room temperature for at least 30 min. before inoculation into a liquid media.

The composition of the liquid media for the production of proteases was either 2% skim milk and 0.17% yeast nitrogen base (Cat. No. 0335-15, obtained from Difco Laboratories, Detroit, MI) or 1% bovine serum albumin (BSA), 1% glucose and 0.17% yeast nitrogen base. The BSA containing mediam was sterilized by passing through a 0.45$\mu$ filter while the skim milk containing media was autoclaved for 30 minutes. 500 ml of each media was inoculated with the spore suspension and the resulting mixture was shaken. Four to five drops of antifoam were used to suppress foaming during shaking. The production of extramycelial proteases was monitored using either N-succinyl-alanyl-alanyl-prolyl-phenylalanine nitroanilide (Delmar et al., Anal Biochem. 99, 316) or azocasein (Charney, J. et al. 1947. J. Biol. Chem. 177, 501) as substrate. It was found that the production of protease was media-dependent. In skim milk media, the largest amount of protease was produced within 8–9 days of culture, while in BSA media the maximum production of protease did not occur until after 14–15 days of culture. In both media, protease activity declined after achieving maximum production level.

EXAMPLE 2

Design and Synthesis of a Probe for Detection oF Subtilisin-Like Genes

Subtilisin-like enzymes share a high degree of sequence homology around their active site serine residue. Serine at position 221 has previously been identified as the reactive serine in serine proteases. Moreover, the assignment of a serine protease to the subtilisin family is based on the amino acid sequence

GLY-THR-SER-MET-ALA

Amino acid sequence alignment of several subtilisin-like enzymes revealed that the homology stretches beyond this sequence as follows:

GLY—THR—SER—MET—ALA—$\frac{\text{SER}}{\text{THR}}$—PHE—HIS—VAL—ALA—GLY—$\frac{\text{LEU}}{\text{ALA}}$—ALA—ALA (Stahl, M. L. et al., 1984, supra; Wells, J. A. et al., 1983, supra; Vasantha, N. et al., 1984, supra; Svendsen, I. et al., 1986, FEBS Letters 196, 228–232; Koide, Y. et al., 1986, J. Bacteriol. 167, 110–116; Kaneda, M. et al., 1984; J. Biochem. 95, 825–825; Jany, K.-D. et al., 1985, Biol. Chem. Hoppe Seyler 366, 485–492). Analysis of the DNA sequences encoding the amino acids in subtilisins also showed high degree of conservation. Based on these observations, the following deoxyoligonucleotide (41-mer) was designed for probing genes that contain similar coding sequences:

GCT GCT AIT CCG GCA ACG TGA GGA GTC
GCC ATG GAC GTT CC 3'

The probe was synthesized using the phosphotriester method of Beaucage et al. (1981, Tetrahedron Letters 22, 1859–1862).

This oligonucleotide probe hybridizes with complementary DNA sequences in the genomic clone or cDNA clone of the serine protease at a temperature range of from 50°–78° C. depending on the number of mismatches. Therefore, when using this probe, it is necessary to include hybridization and washing at several temperatures and salt concentrations for adequate stringency. The 41-mer oligonucleotide may be used for probing genes encoding for subtilisin-like enzymes in genomic and cDNA libraries as well as mRNA encoding subtilisin-like enzymes.

EXAMPLE 3

Construction of the Genomic Library and Isolation of the Gene for Protease TW7

Mycelia were collected on miracloth, as previously described, following 9–15 days of fungal growth. Mycelia were weighed and quickly frozen in dry ice and isopropanol. To 10 g of frozen mycelia was added 10 g of autoclaved alumina and 20 ml of lysis buffer (4% SDS, 20 mM Tris-HCl, pH 7.5, 10 mM EDTA, 0.15M NaCl). The resulting mixture was ground for 5 minutes in a sterile mortar using a pestle. An additional 20 ml of buffer and 40 ml of phenol-chloroform-isoamyl alcohol (25:24:1) was added to the ground mixture and the lysate was shaken for 20–30 min at room temperature and centrifuged for 10 min. The aqueous phase was extracted with phenol and chloroform. Ribonuclease A and proteinase K were added to the lysate to eliminate RNA and protein respectively from the DNA preparation. Ethanol was added to the lysate and DNA was spooled, suspended in TE (20 mM Tris-HCl, pH 8.0, 1 mM EDTA) and stored at 4° C.

A complete digestion of the genomic DNA isolated from *T. album* was conducted using restriction enzymes EcoRI and BamHI to construct a library in plasmid vector pBR322. The vector pBR322 was also digested with the same enzymes and then treated with alkaline phosphatase. Following ligation of the *T. album* DNA fragments with the pBR322 vector, transformation of competent HB101 cells was conducted in accordance with the procedures of Mandel et al., 1970, *J. Mol. Biol.* 53, 159–162. Ampicillin-resistant colonies were probed for the presence of subtilisin-like genes using the 41-mer oligonucleotide probe of Example 2. Colony lift and hybridization was conducted according to the procedures of Grunstein et al., 1975, *Proc. Natl. Acad. Sci. USA*, 72, 3961-3965 except that a gene screen membrane (NEF-972, New England Nuclear) was used instead of nitrocellulose. Filters were processed for DNA denaturation in situ, followed by neutralization, drying and baking at 80° C. in vacuum. Prehybridization was at 55° C. for 3-4 hours in 5X Denhardt's solution containing 200 μg tRNA/ml. Hybridization was carried out at 55° C. for 20 hours in 5× SSC, 1% SDS, 1× Denhardt's solution and 200 μg tRNA/ml. The filters were washed in stringent conditions, 2× SSC at 55° C. until background radioactivity was negligable. A second round of screening of putative positive colonies with the 41-mer oligonucleotide probe was conducted by reinoculating the putative positive clones onto L agar plates containing 50 μg ampicillin/ml and repeating the screening steps described above. Following the second round of screening, only one positive clone was obtained. The positive colony was cultured in Luria broth containing 50 μg ampicillin/ml. From the overnight culture, a plasmid containing the gene for protease TW7 was isolated using the procedures described by Birnboim, *Methods in Enzymol.* 100, 243-154, (1983). For purposes of Southern blotting and extensive restriction mapping, the plasmid was purified using cesium chloride ethidium bromide gradients and ultracentrifugation. A 2.8 kb fragment of *T. album* DNA was found to contain the gene for protease TW7.

Restriction fragments of this plasmid generated by different enzymes were resolved on agarose gels by electrophoresis, transferred onto gene screen plus ® membranes then probed with the 41-mer oligonucleotide probe of Example 2 to identify the fragment containing the complete gene for protease TW7. From this, it was determined that an EcoRI-ClaI fragment containing 1056 nucleotides contained the gene. This fragment was then subcloned in the bacteriophage M13mp18 and M13mp19 for single strand DNA sequencing using the universal primer (Messings, J. 1983; *Methods in Enzymol.* 101C, 20-75). The dideoxy chain termination procedure described by Sanger, F. et al., (1977), *Proc. National Acad. Sci. USA*, 74, 5463 was used for DNA sequencing. Once some partial DNA sequence was obtained, additional oligonucleotide primers were used to complete the sequencing of the two strands of the gene. The nucleotide sequence of the gene thus characterized is represented in FIG. 1. The gene contains 1056 nucleotides and is defined by a site for restriction enzyme EcoRI on the 5' end and a ClaI on the 3' end. Restriction mapping of the fragment reveals the presence of unique sites for the restriction enzymes HindIII, KpnI and BglI. The putative protease encoded by this gene was named protease TW7.

The isolated gene for protease TW7 encoded the complete amino acid sequence of the mature protein and 12 amino acids of a putative "pro" region. The gene encoding the mature protease TW7 is interrupted by two introns. These introns are of 54 and 84 nucleotides in length. The exact position of the introns were determined by comparing the nucleotide sequences of the genomic DNA with that of the cDNA for protease TW7. The two introns begin with the nucleotide sequence GT and end with the sequence AG. TAG is used as the termination codon which is followed by another TAG at an 8 codon interval. The putative processing of mRNA occurs between sequences coding for serine (the last amino acid of the possible pre-pro sequence) and alanine (the first amino acid) of the mature protease TW7.

EXAMPLE 4

Construction of the cDNA Library and Isolation of the cDNA gene for Protease TW7

Although the complete gene encoding the mature protease TW7 was obtained from the genomic library, this gene cannot be used for the expression of the proteolytic enzyme in microorganisms such as *B. subtilis* and *E. coli* because these organisms lack the enzymes for removing the intron sequences from the nascent RNA to form the functional messenger RNA. The isolation of functional messenger RNA from the *T. album* Limber fungus was attempted to obtain a complementary DNA gene, which may be expressed in microorganisms suitable for the production of protease TW7.

*T. album* Limber was grown in the skim milk media described in Example 1 for 9 days, after which mycelia were collected on one layer of miracloth. To about 20 g of freshly harvested mycelia was added 100 g of sterile alumina, 45 ml of lysis buffer (4% SDS, 1 mM EDTA, 100 mM Na acetate, pH 5.0) and 20 ml of phenol:-chloroform:isoamyl alcohol (25:24:1), then mycelia were ground in a sterile mortar with a pestle for 20 min. After addition of 50 ml of buffer and 50 ml of phenol:-chloroform: isoamylalcohol, the lysate was shaken at room temperature for 30 minutes before centrifuging at 5000×g for 15 minutes. Following phenol:chloroform extraction, 0.1 volume of 3M ammonium acetate and 2.5 volumes of ethanol was added and the nucleic acids were allowed to precipitate at −20° C. overnight. The polyadenylated RNA species was isolated using oligo dT-cellulose in accordance with the procedures described by Maniatis et al. (1982, supra). In order to prevent RNA breakdown during the manipulation of samples, all buffers were treated with 0.1% diethyl pyrocarbonate and then autoclaved for 60 minutes. The isolated mRNA population was precipitated with 2.5 volumes of ethanol following the addition 0.1 volumes of 3M ammonium acetate.

Northern blot analysis of the mRNA population was conducted following the glyoxal-DMSO procedure described by Maniatis et al. (1982). The mRNA species were separated on a 1.1% agarose gel, blotted onto a gene screen plus membrane (NEF-976, New England Nuclear) and hybridized with a kinased oligomer probe representing the amino terminus of protease TW7 and having the nucleotide sequence:

5' TGGGGCGTCTTCCTGGGTGGC 3'

The prehybridization and hybridization were carried out at 55° C. followed by stringent washing at 55° C. and 60° C. Upon exposure of the filter to x-ray film, a single mRNA species of about 2000 nucleotide bases long was identified in the mRNA population to contain the sequence coding for protease TW7.

Double stranded cDNA was synthesized on polyA+ mRNA template following the procedures described by Okayama et al., (1982), *Mol. Cell Biol.*, 2, 161-170. Competent *E. coli* HB101 cells were transformed with the plasmid vectors containing the cDNA inserts (Hanahan, 1983, *J. Mol. Biol.* 166, 557-580). Transformed colonies on nitrocellulose filters were replica plated onto a second set of nitrocellulose filters. The master and the replica filters were incubated at 37° C. on L agar plates containing 50 μg ampicillin/ml, until the colonies grew up (generally 2-3 hours for master plates and 5-6 hours for replica). Master filters were stored at 4° C. while the replica filters were incubated overnight on L agar plates containing 100 μg chloramphenicol/ml for plasmid amplification. Replica filters were processed for DNA denaturation, renaturation, baking, prehybridization followed by hybridization with the oligomeric probe as used for the mRNA detection for Northern blot. Following a second series of screening in which the isolated single positive colonies were identified, plasmid DNA was prepared in accordance with the procedures of Birnboim, (1983, supra). Nucleotide sequencing of the positive clones was conducted essentially as described for the genomic clone in accordance with Example 3.

EXAMPLE 5

Characterization of the cDNA Gene for Protease TW7

The nucleotide sequence of the cDNA clone has been determined from single stranded and double stranded DNA. FIG. 2 represents the nucleotide sequence of the cDNA for protease TW7. The sequence is 1016 bases in length and ends with a polyA tail. The restriction map of the clone reveals the presence of an EcoRI site proximal to the 5' end of the sequence coding for the mature, secreted form of the gene product.

The nucleotide sequence of the cDNA clone for the protease TW7 gene is identical to the genomic clone, except for the lack of introns in the cDNA clone.

EXAMPLE 6

Construction of the cDNA Library and Isolation of the cDNA Gene for Protease TW3

The isolation of functional messenger RNA from the *T. album* fungus was attempted to obtain a complementary DNA gene which could be eventually expressed in industrial microorganisms for large scale production of protease TW3.

*T. album* was grown in a BSA media for 15 days after which mycelia were collected on one layer of miracloth. To about 20 g of freshly harvested mycelia 100 g of sterile alumina and 45 ml of lysis buffer (4% SDS, 1 mM EDTA, 100 mM Na acetate, pH 5.0), 20 ml of phenol:chloroform:isoamyl alcohol (25:24:1) were added then mycelia were ground in a sterile mortar with a pestle for 20 min. Following addition of 50 ml of buffer, and 50 ml of phenol:chloroform: isoamylalcohol, the lysate was shaken at room temperature for 30 minutes before centrifuging at 5000×g for 15 minutes. Following extraction with phenol:chloroform, 0.1 volume of 3M ammonium acetate and 2.5 volumes of ethanol were added and the nucleic acids were allowed to precipitate at −20° C. overnight.

The isolation of polyadenylated RNA species was carried out using oligo dT-cellulose in accordance with the procedures described by Maniatis et al. (1982, supra). The isolated mRNA population was precipitated with 2.5 volumes of ethanol following the addition of 0.1 volumes of 3M ammonium acetate.

Northern blot analysis of the mRNA population was conducted following the glyoxal-DMSO procedure described by Maniatis et al. (1982). mRNA species were separated on a 1.1% agarose gel, blotted onto a gene screen plus ® membrane (NEN-976, New England Nuclear) and hybridized with kinased oligomer probes, prepared in Example 2. The prehybridization and hybridization were conducted at 55° C. followed by stringent washing at 55° C. and 60° C. Upon exposure of the filter to x-ray film, a single mRNA of about 2000 nucleotide bases long was identified in the mRNA population to contain the sequence coding for protease TW3.

In order to prevent RNA breakdown all buffers used in these examples were treated with 0.1% diethyl pyrocarbonate and autoclaved for 60 minutes. Double stranded cDNA was synthesized on polyA+ mRNA template following the method of Okayama et al. (1982) *Mol. Cell Biol.*, 2, 161–170. Competent *E. coli* HB101 cells were transformed with the plasmid vectors containing the cDNA inserts, (Hanahan, 1983, *J. Mol. Biol.* 166, 557–580). Transformed colonies on nitrocellulose filters were replica plated onto a second set of nitrocellulose filters. The master and the replica filters were incubated at 37° C. on L agar plates containing 50 μg ampicillin/ml, until the colonies grew up (generally 2-3 hours for master plates and 5-6 hours for replica). Master filters were stored at 4° C. while the replica filters were incubated overnight on L agar plates containing 100 μg chloramphenicol/ml for plasmid amplification.

Replica filters were processed for DNA denaturation, renaturation, baking, prehybridization followed by hybridization with the oligomeric probe used for the mRNA detection for Northern blot. After a second series of screening in which the isolated single positive colonies were identified, plasmid DNA was prepared (Birnboim, 1983, *Methods in Enzymol.* 101C, 20–75). Nucleotide sequencing of the positive clones was carried out as follows: A complete restriction analysis of the clone was followed by subcloning different fragments into M13mp18 and mp19 for single strand DNA sequencing. Double strand sequencing was carried out by the use of sequence-specific primers. The dideoxy chain termination procedure (Sanger, F. et al., 1977, *Proc. Natl. Acad. Science USA,* 74: 5463) was used for DNA sequencing.

EXAMPLE 7

Characterization of the cDNA Gene for Protease TW3

A full length cDNA clone was obtained for the protease TW3. The clone codes for the mature protease as well as the putative prepro region of the protease. There are four ATG in the open reading frame preceding the sequence coding for the mature protein. Most probably the first ATG codes for the initial methionine as it is followed by an area enriched in hydrophobic amino acids (Von Heijne, G. 1986, *Nucleic Acids Res.* 14, 4683–4690). The putative pro region is comprised of about 100 amino acids, a situation very similar to in subtilisin (Stahl et al., 1984 supra).

Figure 9A:
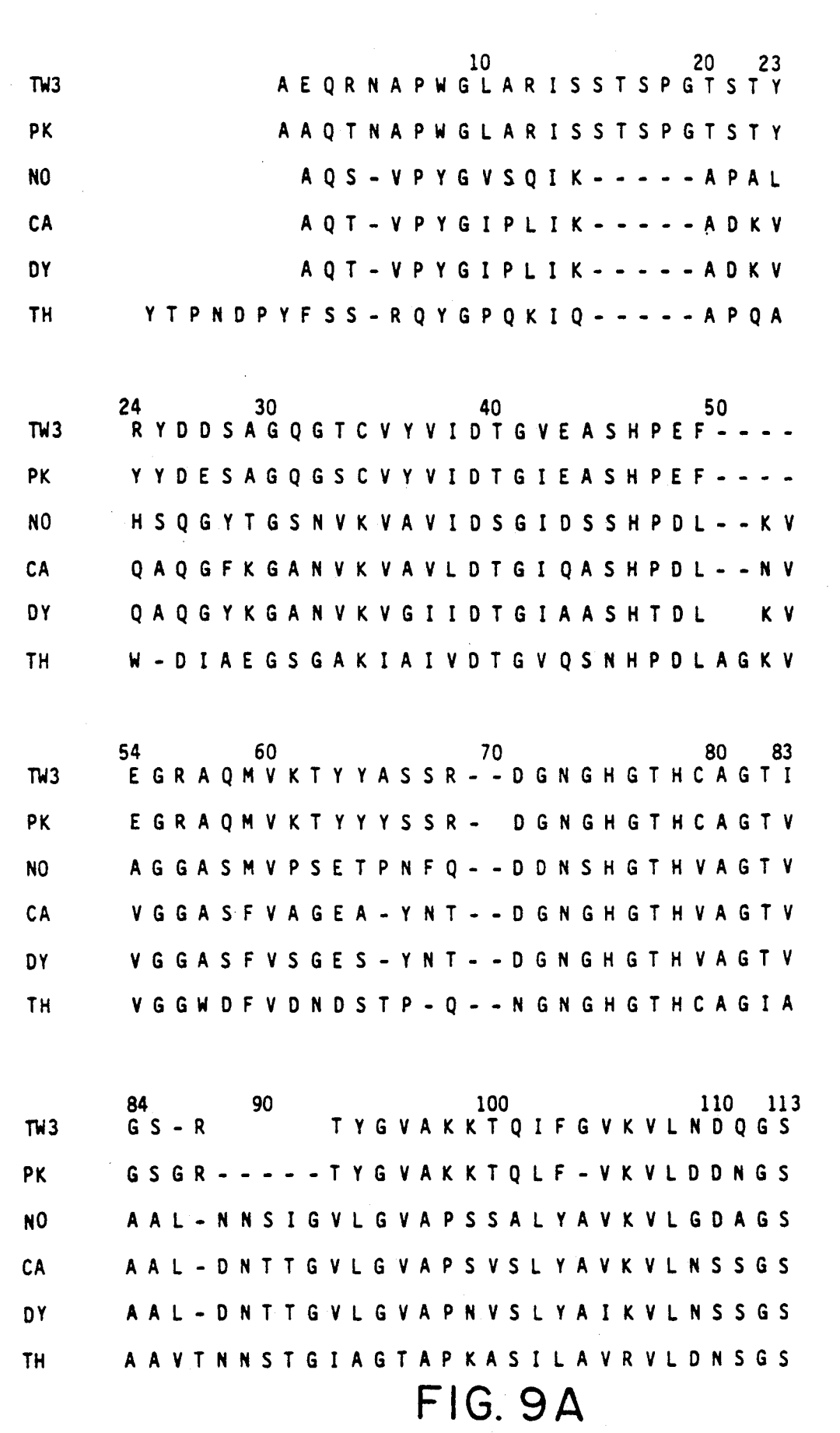
Figure 9B:
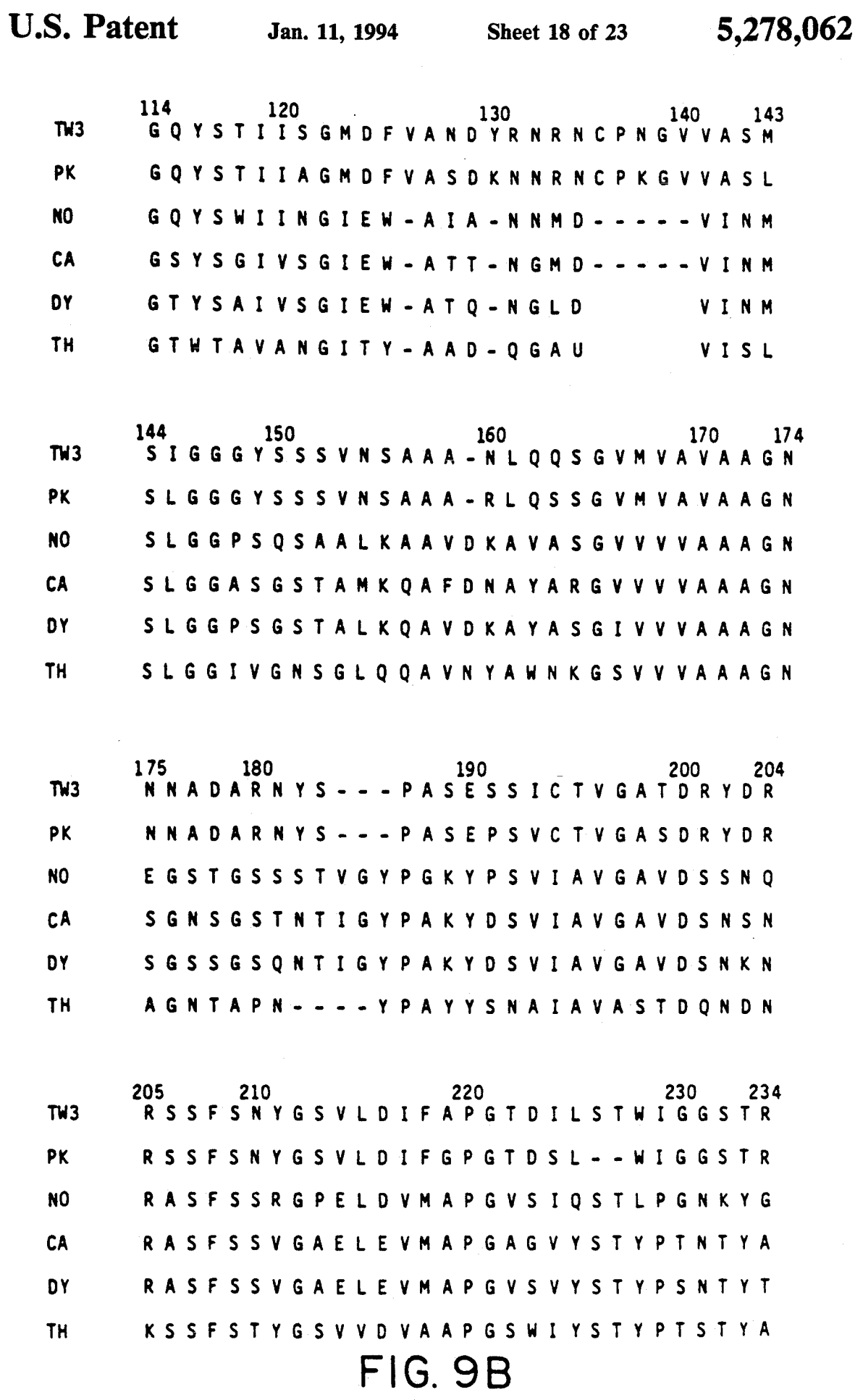
Figure 9C:
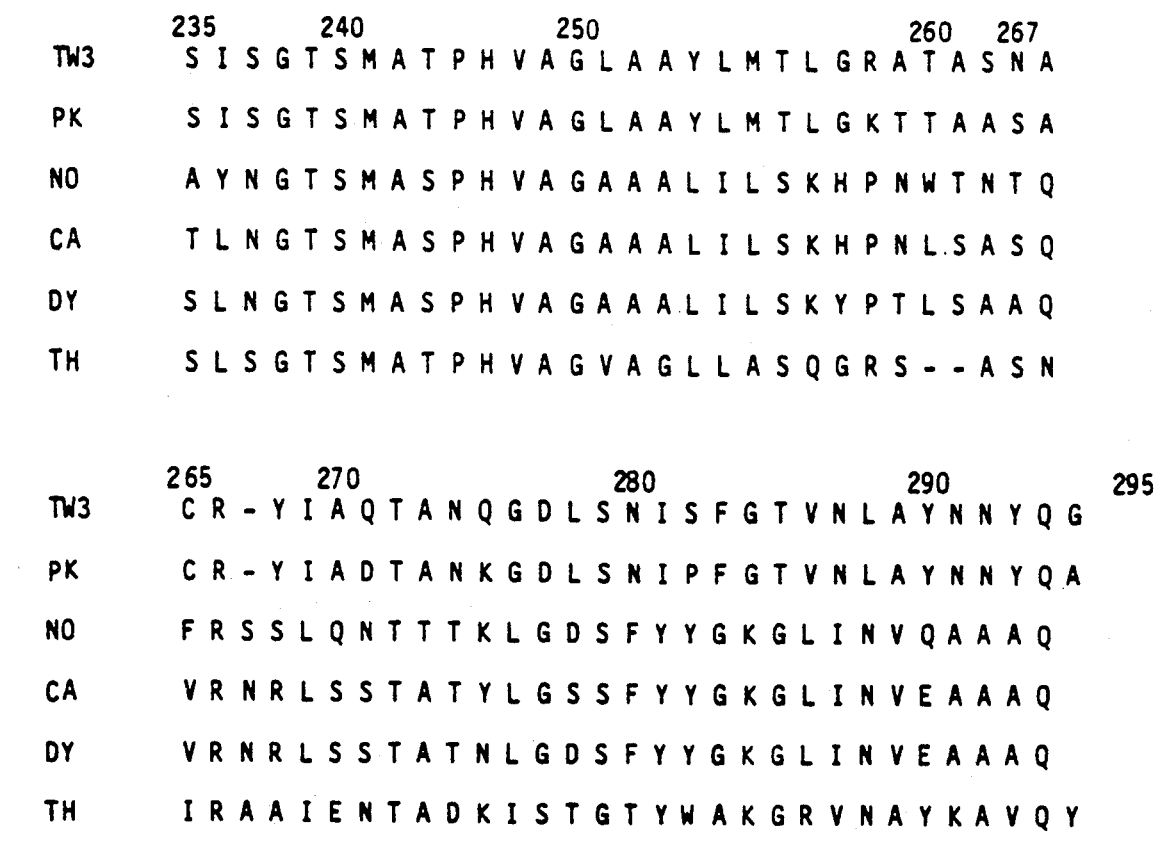

The amino acid sequence of the mature protein as determined from the nucleotide sequence has a large percentage of homology with that of proteinase K. There is approximately 90% homology between these two proteases. There are certain positions where the amino acid resembles that in subtilisins, but not to proteinase K. For example, at positions 143, a methionine residue occurs in all subtilisins as well as in protease TW3, while a leucine residue is present at that position in proteinase K. Similarly at position 219, an alanine residue is present in protease TW3 and subtilisins, but not in proteinase K. In addition, the amino acid fragment, Ser-Thr-, is absent from proteinase K while being present in all others in FIG. 9 at position 226 and 227.

EXAMPLE 8

Determination of Proteolytic Activity

The proteolytic activity of serine proteases in the following Examples was determined using azoalbumin as a substitute. Aliquots (20 μl) of enzyme solution or enzyme buffer (for controls) were mixed with 1 ml of 0.6% azoalbumin in 0.05M Tris-HCl pH 8.2 (unless otherwise mentioned) and the hydrolytic reaction was conducted at room temperature. The reaction was terminated after 20 min. upon addition of 10% trichloracetic acid (400 μl). The hydrolysate was separated from the precipitated protein by centrifugation and its optical density at 410 nm, as compared to the control was measured.

Protease activity was also assayed using azocasein as the substrate. To a final volume of 500 μl, 20 μl of azocasein (5% solution in 0.2M Tris-HCl, pH 7.5, 1mM $CaCl_2$), 20 μl of enzyme (1-10 μg) and 460 μl of 50 mM Tris-HCl, pH 7.5 were added. The samples were incubated at 37° C. for 30 min. Following incubation, 500 μl of 10% TCA was added to the samples and the samples were incubated on ice for 15 min. After centrifugation for 2 min. 800 μl of supernatant was added to a tube containing 200 μl of 1.8N NaOH. The optical density of the sample was then measured at 420 nm against the control.

EXAMPLE 9

Isolation and Purification of Protease TW7 from the Culture Broth of *Tritirachium album* Limber Protease TW7 was separated and purified from the extracellular media of the *T. album* culture. A 0.5 liter aliquot of the *T. album* culture broth obtained after 15 days of fermentation in the BSA-glucose media described in Example 1 was centrifuged for 10 min. Proteins in the clear supernatant were precipitated using ammonium sulfate (180 g) and collected by centrifugation. The precipitate was suspended in 0.02M sodium phosphate, pH 6.0 (50 ml) and insoluble material was removed by centrifugation. The proteins in the supernatant were reprecipitated with acetone (2.5 volumes). The precipitate was collected by centrifugation and collected on a sintered glass funnel. The precipitate was then dissolved in water (40 ml) and the resulting solution was dialyzed at 4° C. against 0.02M sodium phosphate at pH 6.0. The dialyzed solution was cleared by centrifugation and then passed through a column (2.5×10 cm) of carboxylmethylcellulose (CM-52, Whatman) at a rate of 2 ml per minute, followed by washing the column with 0.02M sodium phosphate pH 6.0 (30 ml). The flow through and washing solutions were combined and the proteins were precipitated by adding 2.5 volumes of acetone. The precipitate was separated by centrifugation, filtered, and dried under vacuum. The acetone powder (185 mg) was dissolved in 0.02M sodium acetate pH 5.0 (2 ml) and loaded onto a Sephadex G-75 molecular sieve column (2.5×90 cm). Fractionation on the molecular sieve column was conducted with 0.02M sodium acetate pH 5.0 at a flow rate of 6 ml per hour. Fractions of 2 ml were collected and monitored for u.v. absorbance at 275 nm. Of the three major peaks that were eluted from the column, only one showed proteolytic activity in hydrolyzing the chromogenic protein-substrate azoalbumin. The enzyme in this peak (between 102-110 ml) was precipitated with acetone (2.5 volumes) and collected by centrifugation. The precipitate was dissolved in 2 mM calcium acetate (20 ml) and the solution was dialyzed at 4° C. against water, and then lyophilized. SDS-PAGE of reduced sample demonstrated protease TW7 as one major band (>95%) with an apparent molecular weight of 35,000 daltons.

EXAMPLE 10

Amino Terminus Analysis of Protease TW7

Protease TW7 was purified from the culture supernatant as described in Example 9. The purified protein was then inactivated with PMSF (phenylmethylsulfonylfluoride) and further purified using HPLC. The amino terminus was determined by reconstituting the protein in trifluoroacetic acid (TFA) containing 1 mM PMSF. Automated gas phase Edman degradation was carried out for the amino terminus analysis and the amino terminus was determined to be Ala-Thr-Gln-Glu-Asp-Ala-Pro-Trp-Leu-Ala-Arg-Ile-Ser-Ser.

EXAMPLE 11 pH-Profile of Proteinase TW7

The pH-profile of proteinase TW7 at 25° C. was determined using azoalbumin as a substrate. Sustrate solutions containing 0.6% azoalbumin in sodium phosphate-sodium borate buffers covering the pH range between 5.0 and 12.75 were prepared. To the azoalbumin solutions was added either 10 μl of a 1 mg/ml solution of proteinase TW7 in water or 10 μl of water (control) and the proteolytic activity of each solution was determined as described in Example 8. The pH-profile of proteinase TW7 is represented in FIG. 5 wherein the percentage of maximum proteolytic activity has been plotted versus pH. The optimum pH range of proteinase TW7 has been determined to be betweena pH range of from 9 to 11.

EXAMPLE 12

Temperature Profile of Proteinase TW7

The temperature profile of proteinase TW7 in 0.05 sodium phosphate at pH 8.5 was determined by measuring the proteolytic activity over a temperature range of between 20° C. and 70° C. Aliquots (1 ml) of 0.6% azoalbumin in 0.05M sodium phosphate pH 8.5 were incubated at various temperatures and after the addition of the enzyme solution (20 μl of 0.5 mg proteinase TW7 per ml of the same buffer) or 20 μl of buffer (control) the reaction was allowed to proceed for 10 minutes and then terminated upon addition of 10% trichloroacetic acid (400 μl). The temperature profile of proteinase TW7 is represented in FIG. 6 wherein the percentage of maximum enzyme activity has been plotted versus temperature. As illustrated in FIG. 6, the preferred temperature of proteinase TW7 ranges between 57° C. to 62° C.

EXAMPLE 13

Determination of Protease Stability in the Presence of Detergent

The stability of protease TW7 was compared in detergent as well as non-detergent solutions with that of subtilisin Carlsberg and to that of proteinase K. Solutions of the enzymes to be evaluated were prepared in appropriate buffers so that the initial proteolytic activities of the various enzyme solutions were similar as measured by the azoalbumin assay described in Example 8. The solutions were incubated at 52° C. and aliquots were drawn and measured for residual enzyme activity. The results obtained are represented in Tables 1 and 2. The residual enzyme activity is expressed as a percent of the initial enzyme activity.

TABLE 1

Stability of protease TW7 vs. proteinase K and subtilisin Carlsberg in 0.1M sodium phosphate pH 8.0 with and without SDS.

| Protease | 0 Hours | 1 Hour | 2 Hours | 24 Hours |
|---|---|---|---|---|
| Without SDS: | | | | |
| Protease TW7 | 100% | 106% | 102% | |
| Proteinase K | 100% | 67% | 43% | |
| Subtilisin Carlsberg | 100% | 29% | 8% | |
| With 0.5% SDS: | | | | |
| Protease TW7 | 100% | 99% | 99% | 92% |
| Proteinase K | 100% | 32% | 9.5% | 0% |
| Subtilisin Carlsberg | 100% | 5% | 0% | 0% |

TABLE 2

Stability of protease TW7 vs. Subtilisin Carlsberg in 0.1M sodium glycinate pH 10.30 containing 0.5% SDS

| Protease | t = 0 | t = 1 Hr. | t = 18 Hr. | $T_{\frac{1}{2}}$ |
|---|---|---|---|---|
| Protease TW7 | 100% | 105% | 80% | 5.6 Hr. |
| Subtilisin Carlsberg | 100% | 11.3% | 0% | 0.3 Hr. |
| Subtilisin BPN | 100% | 6.6% | 0% | 0.25 Hr. |

EXAMPLE 14

Stability of Protease TW7 in Detergent Compositions

The stability of protease TW7 and proteinase K were evaluated in three enzyme-containing commercial laundry detergents, Era Plus ® (manufactured by Procter and Gamble), Tide ® (manufactured by Procter and Gamble) and Dynamo ® (manufactured by Colgate-Palmolive). The concentrated stock detergents were diluted ten times in deionized water. The endogenous protease was inactivated by incubating the diluted detergent at 65° C. for 1 hour prior to addition of the protease to be evaluated. The relative activity of the protease to be evaluated in each detergent formulation was adjusted to be similar to the enzymatic activity present in the original detergent formulation.

Deactivated detergent containing the proteases to be evaluated were incubated at 52° C. along with the detergent containing active endogenous enzyme. The residual proteolytic activity after different incubation periods were quantitated by withdrawing samples and assaying in accordance with the procedures as described in Example 8.

Protease TW7 was found to be stable in all detergent formulations tested. For example, in a formulation containing deactivated Era Plus ®, protease TW7 retains 100% of the enzyme activity after 6 hours of incubation compared to only 12% of the endogenous enzyme. In a formulation containing deactivated Dynamo ®, protease TW7 retained 76% of the enzyme activity after 29 hours of incubation.

The stability of the protease TW7 was also tested in a formulation containing the laundry detergent Wisk ® which does not contain enzymes in its formulation. Following a 1:10 dilution of the stock detergent in deionized water, proteinase K or protease TW7 were added and the resulting composition was incubated at 52° C. for various durations. The remaining activity was assayed using the procedures described in Example 8. Protease TW7 was more stable than proteinase K, as illustrated in Table 4, wherein after 3.5 hours of incubation, proteinase K retained only 20.1% of the original activity while protease TW7 retained approximately 90% of its original enzymatic activity.

TABLE 3

| Detergent Formulation (Enzyme) | 3 h | 6 h | 1 h | 2 h | 24 h | 29 h | 1.3 hr | 3.5 hr |
|---|---|---|---|---|---|---|---|---|
| Era Plus ® | | | | | | | | |
| (Protease TW7) | 95 | 90 | | | | | | |
| (Proteinase K) | 79 | 64 | | | | | | |
| (Endogenous enzyme) | 36 | 11 | | | | | | |
| Tide ® | | | | | | | | |
| (Protease TW7) | | | 107 | 104 | 64 | | | |
| (Proteinase K) | | | 58 | 23 | 0 | | | |
| Dynamo ® | | | | | | | | |
| (Protease TW7) | | | | | | 76 | | |
| (Proteinase K) | | | | | | 34.4 | | |
| (Endogenous enzyme) | | | | | | 22 | | |
| Wisk ® | | | | | | | | |
| (Protease TW7) | | | | | | | 95.7 | 89.5 |
| (Proteinase K) | | | | | | | 44.3 | 20.1 |

Experiments were carried out as described in Example 14. Percentage of the original activity remaining after different time points are depicted.

EXAMPLE 15

Expression of Proteinase TW7

An oligonucleotide adaptor was synthesized to insert the gene coding the mature protease TW7 in the expression vector pCFM 1156 for expression in *E. coli*. The adaptor has the following sequence:

```
AATTCTAGAAGGAGGAATAACATATGGCCACCCAGGAAGACGCCC
    GATCTTCCTCCTTATTGTATACCGGTGGGTCCTTCTGCGGGGTAC
```

The construction of the recombinant plasmid for expression in *E. coli* involved the following steps:
(1) Construction of a double-stranded oligonucleotide, which contains the portion of the expression vector pCFM 1156 from the XbaI site up to the NdeI site including the ATG sequence, followed by the amino terminal sequence of the mature protease TW7 gene starting from GCC up to the first NcoI site. Additional nucleotides were added on the 5' end to obtain an extra EcoRI site that will facilitate the construction.

Figure 12A:
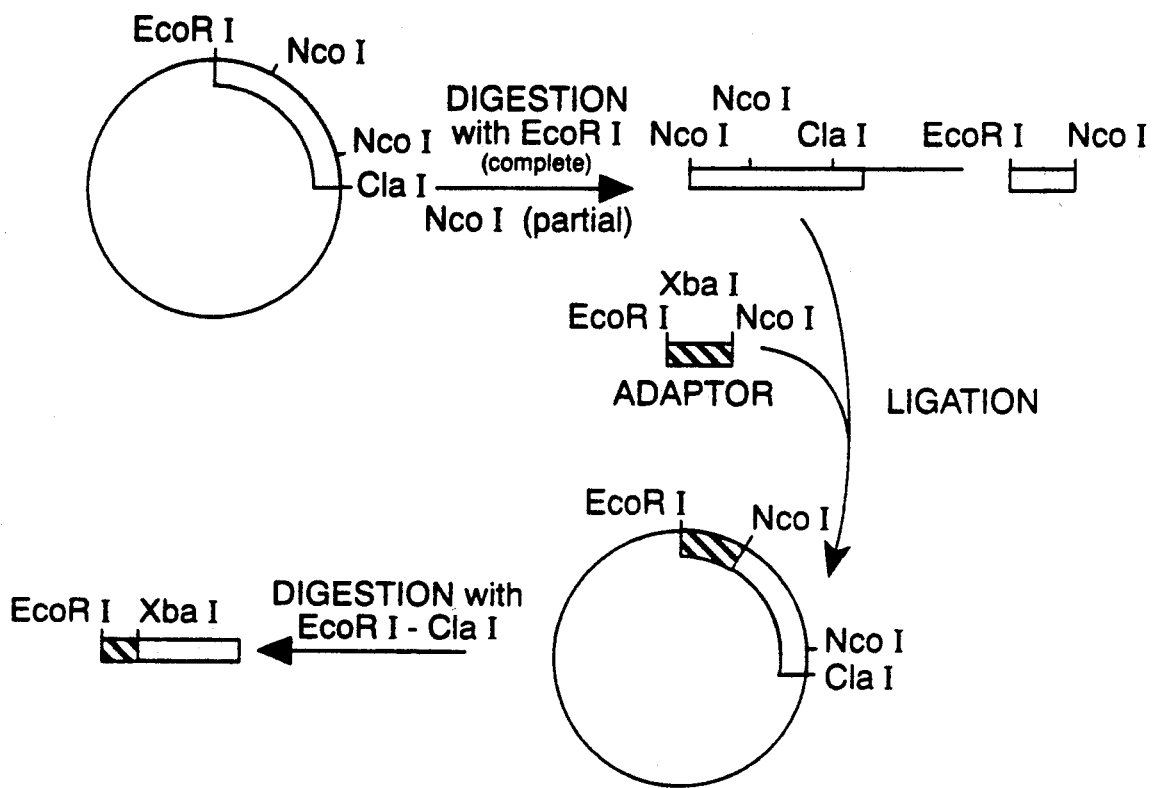
Figure 12B:
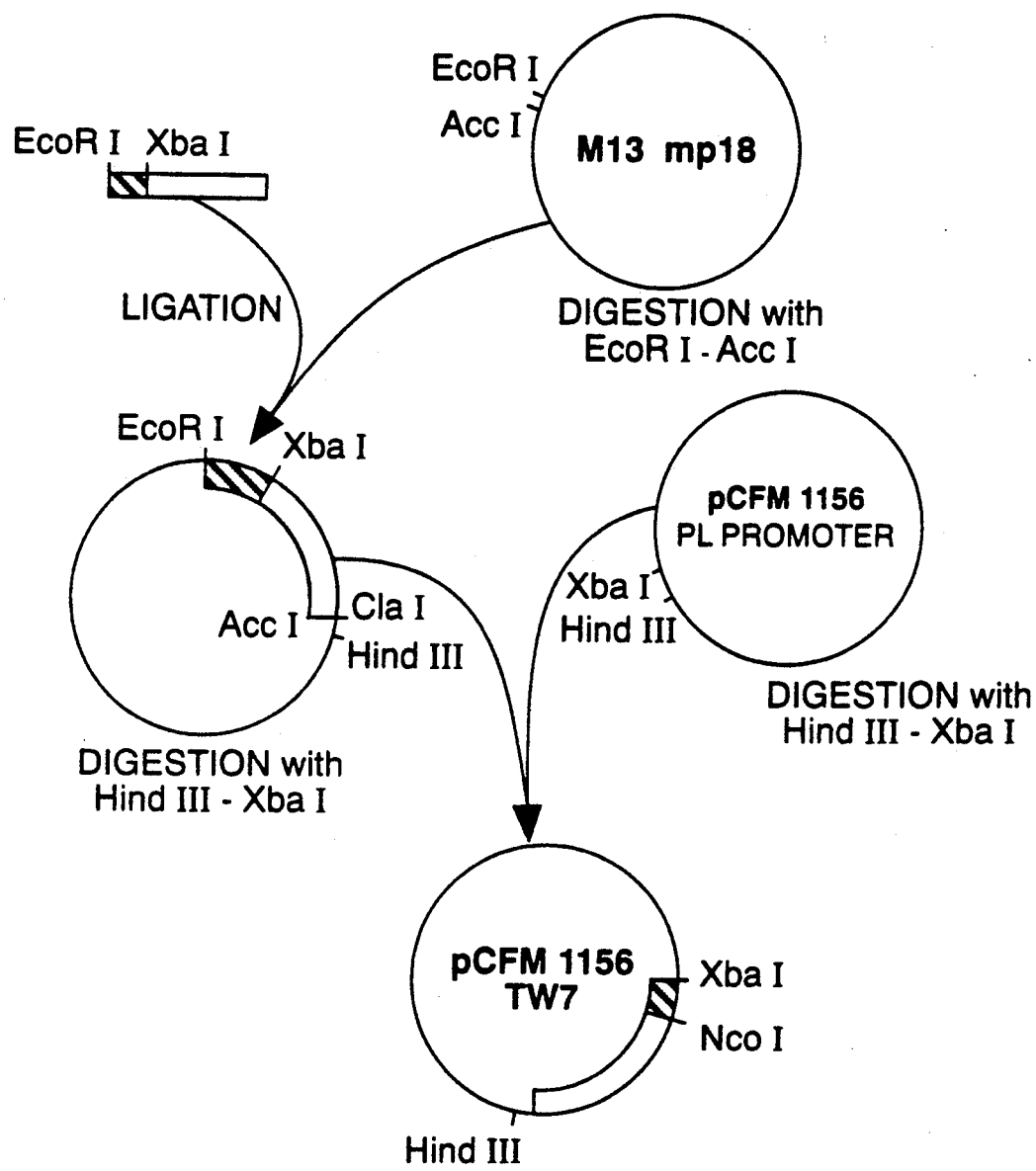

(2) As illustrated in the FIG. 12, the cDNA for protease TW7 was digested completely with the restriction enzyme EcoRI and partially with NcoI to obtain the large EcoRI-NcoI fragment, to which kinased EcoRI-NcoI, adapter was ligated to obtain a cDNA gene for protease TW7 with the adaptor.

(3) The reconstructed cDNA for protease TW7 was then digested with EcoRI and Cla to obtain the gene for the protease TW7, which was inserted into M13mp18 which was already digested with EcoRI and AccI.

(4) The M13mp18 containing the protease TW7 gene was digested with the restriction enzymes XbaI and HindIII to rescue the protease TW7 gene.

(5) The expression vector pCFM 1156 was also digested with the restriction enzymes XbaI and HindIII to insert the protease TW7 gene obtained from M13 mp18 as a XbaI and HindIII fragment.

The resulting recombinant expression plasmid thus constructed contained a pL promoter, a Shine Dalgarno sequence, an ATG followed by the nucleotide sequence coding for the mature protease TW7 protein.

Competent *E. coli* FMII cells (ln−, ptr3−) were transformed with this recombinant plasmid.

Plasmid DNA was isolated from the transformed cells and the positive clones were identified by digesting the plasmid DNA with XbaI and HindIII. One of the positive clones was grown overnight to inoculate a medium of Luria broth containing 20 μg kanamycin/ml. Cells were grown at 30° C. up to an optical density of 0.25 at 600 nm. The temperature of incubation was then shifted to 42° C. for 2 hours for the induction of plasmid born gene products.

E. coli cells were collected by low speed centrifugation. The pellet was weighed and then suspended in 10 volumes of 50 mM Tris-HCl, pH 7.5. The cells were lysed by three passes through a French press. The pellet fraction obtained after another centrifugation was extracted with 5M urea, 50 mM Tris-HCl, pH 8.0. The urea soluble proteins were analyzed using various techniques.

The proteins were reduced with β mercaptoethanol and electrophoresed in a 10% polyacrylamide gel in the presence of SDS. A unique 35,000 dalton protein was the major band present in the urea soluble fraction derived from *E. coli* harboring the recombinant plasmid but not the vector alone. It comigrated with the protease TW7 purified from *T. album*. This protein also reacted specifically with the antibody raised against the fungal protease TW7 in a Western blot analysis. This protein was isolated from polyacrylamide gel to identify the sequences in the amino terminal region, which matched with that of the fungal protease TW7.

The recombinant protease TW7 is enzymatically inactive when isolated from *E. coli* prior to refolding. For reactivation, the protein was suspended in 8M urea, 10 mM DTT, 25 mM Tris-HCl, pH 8.5 in a final concentration of 1 mg protein per ml and then bound to DE52 resin preequillibrated with 25 mM Tris-HCl, pH 8.5 at room temperature. Urea was removed by washing the resin with the same buffer without and then with 4 mM glutathione (reduced) and 0.4 mM glutathione (oxidized). After overnight incubation of the resins in the presence of the above reagents, i.e., 25 mM Tris-HCl, pH 8.5, 4 mM glutathione (reduced) and 0.4 mM glutathione (oxidized), the protein was eluted from the column with 50 mM Tris-HCl, pH 7.5 conaining 0.3M NaCl and precipitated with 3 volumes of acetone. This renatured protein had protease activity against the chromogenic substrate (Example 1) and casein.

EXAMPLE 16

Isolation and Purification of Proteinase TW3 from the Culture Broth of *Tritirachium album* Limber 0.5 liter of *Tritirachium album* Limber culture broth obtained after 15 days of fermentation in the BSA-glucose media described in Example 1 was centrifuged at 15,000 g for 10 min. Proteins in the clear supernatant were precipitated with ammonium sulfate (180 g) and collected by centrifugation. The precipitate was suspended in 0.02M sodium phosphate pH 6.0 (50 ml) and following removal of insoluble material by centrifugation the proteins in the supernatant were reprecipitated with acetone (2.5 volumes). The precipitate was collected by centrifugation and collected on a sintered glass funnel. The precipitate was dissolved in water (40 ml) and the solution was dialyzed at 4° C. against 0.02M sodium phosphate at pH 6.0. The dialyzed solution was cleared by centrifugation and passed through a column (2.5×10 cm) of carboxylmethyl-cellulose (CM-52, Whatman) at a rate of 2 ml per minute, followed by washing the column with 0.02M sodium phosphate pH 6.0 (30 ml). The flow through and washing solutions were combined and the proteins were precipitated by adding 2.5 volumes of acetone.

Elution from the CM-52 column was accomplished with a linear gradient of 0 to 0.4M NaCl in sodium phosphate pH 6.0. Fractions were assayed spectrophotometrically (at 420 nm) for proteolytic activity at pH 8.2 as described in Example 8. Peak fractions containing the enzyme activity were pooled, dialyzed at 4° C. against water and then lyophilized. SDS-PAGE of 2-mercaptoethanol treated sample showed protease TW3 as a major band (>96% based on Coomassie blue staining) having an apparent molecular weight of 31,000 daltons.

EXAMPLE 17

Amino Terminus Analysis of Protease TW3

Protease TW3 was purified from the culture supernatant as described in Example 16. Purified protein was then inactivated with PMSF (phenylmethylsulfonyl-fluoride) and further purified using HPLC. The amino terminus was determined by reconstituting the protein in 50% trifluoroacetic acid (TFA) containing 1 mM PMSF. Automated gas phase Edman degradation was carried out for the amino terminus analysis. The amino terminus was found to be Ala-Glu-Gln-Arg-Asn-Ala-Pro-Trp-Gly-Leu-Ala-Arg-Ile-Ser-Ser-Thr.

EXAMPLE 18 pH-Profile of Proteinase TW3

The pH-profile of protease TW3 at 25° C. was determined using azocasein as a substrate. Sustrate solutions (0.6%) M buffers covering the pH range of between 5.0 and 10 were made. To these azocasein solutions either 20 μl of an 1 mg/ml solution of protease TW3 in water or 20 μl of water (control) was added and the proteolytic activity was determined as described in Example 8. The pH-profile of proteinase TW3 is represented in FIG. 10 wherein the percentage of maximum activity is plotted versus pH. The pH optimum of protease TW3 was determined to be pH 9.

EXAMPLE 19

Temperature Profile of Proteinase TW3

The temperature profile of protease TW3 in 0.05 sodium phosphate at pH 8.5 was determined from the proteolytic activity (azocasein assay) in the temperature range between 4° C. and 65° C. For these measurements, aliquots (1 ml) of 0.6% azocasein in 0.05M sodium phosphate pH 8.5 were incubated at various temperatures and following the addition of the enzyme solution (20 μl of 0.5 mg proteinase TW3 per ml of the same buffer) or 20 μl of buffer alone (control) the reaction was allowed to proceed for 10 minutes and then terminated upon addition 10% trichloroacetic acid (400 μl). The temperature profile of protease TW3 is represented in FIG. 11 wherein the percentage of maximum proteolytic activity has been plotted versus temperature. As illustrated in FIG. 5, the optimum temperature of protease TW3 ranges between 55° C. to 60° C.

EXAMPLE 20

Comparative Stability Study of the Protease TW3 and Subtilisin

Protease TW3 and a commercial subtilisin (Sigma, protease VII, Cat. No. 5255) were tested for their stability at 52° C. in the absence of substrates. Tests were carried out at three different pH values (4.0, 8.0 and 10.0).

Approximately 0.2 mg of enzyme/ml was incubated at 50° C. The remaining activity after a defined time interval was quantitated by withdrawing 10 μl of sample and assaying the proteolytic activity as outlined in Example 8. Table 4 represents the results obtained. The data represents the retained enzymatic activity as a percent of the original enzymatic activity. Protease TW3 demonstrated the best stability. For example, at pH 8.0, after one hour of incubation at 50° C., 90% of the original activity of protease TW3 was retained, while only 2% of the original activity of subtilisin was retained. Following 2 hours of incubation, 96% of protease TW3 activity remained, compared to 0.6% of the activity of the subtilisin. Protease TW3 was also more stable than subtilisin at pH 4.0 and 10.0.

TABLE 4

| Enzyme | Time | | |
|---|---|---|---|
| | 1 h | 2 h | 3 h |
| pH 8.0: | | | |
| TW3 | 89.5 | 96.3 | 87.4 |
| Subtilisin | 2.1 | 0.6 | 0.8 |
| pH 10.0: | | | |
| TW3 | 96.8 | 82.7 | 74 |
| Subtilisin | 30.5 | 9.8 | 3.5 |
| pH 4.0: | | | |
| TW3 | 49.3 | 36 | 20.5 |
| Subtilisin | 0 | 0 | 0 |

EXAMPLE 21

Stability of Protease TW3 in Commercial Laundry Detergents

The stability of protease TW3, as well as of subtilisin were tested in three enzyme-containing commercial laundry detergents. These were Era Plus ® (manufactured by Procter and Gamble), Tide ® (manufactured by Procter and Gamble) and Dynamo ® (manufactured by Colgate-Palmolive). The concentrated stock detergents were diluted 200 fold in deionized water. The endogenous protease was inactivated by incubating the diluted detergent at 65° C. for 1 hour, prior to adding either protease TW3, protease TW7, proteinase K or subtilisin to achieve the enzyme activity present in the original detergent formulation.

Inactivated detergent with added proteases was incubated at 50° C. for various time points along with the detergent containing active endogenous enzyme. The residual proteolytic activity remaining after different incubation periods was quantitated by withdrawing samples and assaying in accordance with the procedures described in Example 8.

As illustrated in Table 5, protease TW3 is very stable in all detergent formulations tested. For example, in a formulation containing Era Plus ®, 94% of its activity was retained after 1 hour of incubation while the formulation containing endogenous enzyme was completely inactivated. In a formulation containing Dynamo, 80% of the activity of protease TW3 remained after one hour of incubation, compared to only a nondetectable level of activity in a formulation containing endogenous enzyme. In a formulation containing Tide ®, 48% of the original activity of TW3 was retained, while 23% of the activity in the formulation containing endogenous enzyme remained after one hour. In all instances subtilisin was inactivated within one hour.

The stability of the protease TW3 was also tested in the laundry detergent Wisk ® which does not contain enzyme in its formulation. Following a 1:200 dilution of the stock detergent in deionized water, subtilisin or protease TW3 were added to the diluted detergent and the samples were incubated at 50° C. The proteolytic activity was assayed using the procedure outlined in Example 8. The results obtained are represented in Table 5.

TABLE 5

| Detergent Formulation | Time | | | |
|---|---|---|---|---|
| (Enzyme) | 10' | 20' | 30' | 60' |
| ERA Plus ® | | | | |
| (TW7) | 83.4 | 94.5 | 87.7 | 89 |
| (TW3) | 87.7 | 89.1 | 92.2 | 94.8 |
| (Subtilisin) | 3.9 | 1.3 | 1.5 | 1.8 |
| (Endogenous enzyme) | 50.0 | 37.7 | 24.7 | 0 |
| (Proteinase K) | 83.2 | 84.1 | 86.7 | 79.7 |
| Tide ® | | | | |
| (TW7) | 103.5 | 111 | 99.6 | 110 |
| (TW3) | 78 | 55.7 | 68 | 48 |
| (Subtilisin) | 1.8 | 0.8 | 0.74 | 0.5 |
| (Endogenous enzyme) | 22.6 | 22 | 21.9 | 23.5 |
| (Proteinase K) | 83 | 75 | 62 | 35.4 |
| Dynamo ® | | | | |
| (TW7) | 84.9 | 90 | 85.9 | 89.3 |
| (TW3) | 83 | 90.8 | 82 | 87.5 |
| (Subtilisin) | 30 | 10.8 | 3.6 | 0.5 |
| (Endogenous enzyme) | 52 | 32.5 | 15.1 | 0 |
| (Proteinase K) | 81.3 | 83 | 79.9 | 87.4 |
| Wisk ® | | | | |
| (TW7) | 89.1 | 87.1 | 90.8 | 90 |
| (TW3) | 58.3 | 43.5 | 28.2 | 6 |
| (Subtilisin) | 21 | 36 | 0.7 | 0.5 |
| (Endogenous enzyme) | 0 | 0 | 0 | 0 |
| (Proteinase K) | 57.6 | 39.7 | 19.7 | 2.8 |

Various other examples and modifications of the foregoing description and examples will be apparent to a person skilled in the art after reading the present disclosure without departing from the spirit and scope of the invention, and it is intended that all such examples or modifications be included within the scope of the appended claims.

What is claimed is:

1. Purified and isolated serine protease TW7.
2. Purified and isolated serine protease TW3.
3. A serine protease according to claim 1 having an amino acid sequence as set forth in FIG. 3.
4. A serine protease according to claim 2 having an amino acid sequence as set forth in FIG. 8.
5. A serine protease according to either of claims 3 or 4 having an amino terminal residue at Ala$^1$.
6. A serine protease having an amino acid sequence of protease TW3 or protease TW7 which is the product of procaryotic or eucaryotic expression of an exogenous DNA sequence.
7. A serine protease according to claim 6 wherein the exogenous DNA is a cDNA sequence.
8. A serine protease according to claim 6 wheien the exogenous DNA sequence is a genomic DNA sequence.
9. A serine protease according to claim 6 wherein the exogenous DNA sequence is a chemically synthesized DNA sequence.
10. A serine protease accoridng to claim 6 having an amino acid sequence as set forth in FIG. 3 or FIG. 8.
11. A serine protease according to claim 6 which is the product of E. coli expression.
12. A serine protease according to claim 6 which is TW3 or TW7.
13. A composition comprising an effective amount of protease TW3 or protease TW7 in a detergent formulation.
14. A composition according to claim 13 wherein the effective amount is at least 0.1 Anson unit of protease activity per 100 g of composition.

* * * * *